US010401371B2

(12) United States Patent
Choi et al.

(10) Patent No.: US 10,401,371 B2
(45) Date of Patent: Sep. 3, 2019

(54) METHOD OF MEASURING CHOLESTEROL LEVELS BY USING IMMUNOGENIC METHOD

(71) Applicant: Boditech Med Inc., Chuncheon-si, Gangwon-do (KR)

(72) Inventors: Eui Yul Choi, Chuncheon-si (KR); Do Won Kim, Chuncheon-si (KR)

(73) Assignee: Boditech Med Inc., Chuncheon-si, Gangwon-do (KR)

( * ) Notice: Subject to any disclaimer, the term of this patent is extended or adjusted under 35 U.S.C. 154(b) by 0 days.

(21) Appl. No.: 15/545,656

(22) PCT Filed: Jan. 22, 2016

(86) PCT No.: PCT/KR2016/000689
§ 371 (c)(1),
(2) Date: Jul. 21, 2017

(87) PCT Pub. No.: WO2016/117956
PCT Pub. Date: Jul. 28, 2016

(65) Prior Publication Data

US 2018/0017587 A1 Jan. 18, 2018

(30) Foreign Application Priority Data

Jan. 23, 2015 (KR) ........................ 10-2015-0011355
Jan. 22, 2016 (KR) ........................ 10-2016-0007850

(51) Int. Cl.
*G01N 33/53* (2006.01)
*G01N 33/92* (2006.01)

(52) U.S. Cl.
CPC ..... *G01N 33/92* (2013.01); *G01N 2333/3156* (2013.01)

(58) Field of Classification Search
CPC . G01N 2333/3156; G01N 33/92; G01N 33/53
See application file for complete search history.

(56) References Cited

U.S. PATENT DOCUMENTS

2003/0003501 A1* 1/2003 Fitzpatrick ............. G01N 33/92 435/7.1
2007/0207515 A1 9/2007 Matsumoto et al.

FOREIGN PATENT DOCUMENTS

| | | | |
|---|---|---|---|
| EP | 1 418 429 | A1 | 5/2004 |
| JP | 2000-325097 | A | 11/2000 |
| JP | 2002-539458 | A | 11/2002 |
| KR | 10-2004-0025931 | A | 3/2004 |
| KR | 10-2007-0011416 | A | 1/2007 |
| KR | 10-2010-0091176 | A | 8/2010 |
| WO | 00/55635 | A1 | 9/2000 |

OTHER PUBLICATIONS

Kwiatkowska et al., Orphanet Journal of Rare Diseases 2014, 9:64.*
Ohno-Iwashita, chapter 25 Cholesterol-binding toxins and anti-cholesterol antibodies as structural probes for cholesterol localization, Subcell Biochem 2010, 51:597-621.*
Notice of Final Rejection, dated Dec. 10, 2018, with machine translation.
Kwiatkowska et al., "Visualization of cholesterol deposits in lysosomes of Niemann-Pick type C fibroblasts using recombinant perfringolysin O", Orphanet Journal of Rare Diseases, (2014), vol. 9, No. 1, 64—16 pages.
Wade et al., "Mouse, but Not Human, ApoB-100 Lipoprotein Cholesterol Is a Potent Innate Inhibitor of *Streptococcus pneumoniae* Pneumolysin", PLoS Pathog, (2014), vol. 10, No. 9, e1004353—12 pages.

* cited by examiner

*Primary Examiner* — Julie Wu
*Assistant Examiner* — Carmencita M Belei
(74) *Attorney, Agent, or Firm* — Vorys, Sater, Seymour & Pease LLP; Min Suhn Koh

(57) ABSTRACT

Disclosed is a method for measuring cholesterol by using a cholesterol dependent cytolysin (CDC), which is a cholesterol binding protein, and an antibody specifically recognizing HDL-C or LDL-C. The method according to the present application is capable of rapidly measuring low density lipoproteins and high density lipoproteins at low cost, and thus can be effectively applied in various fields requiring the measurement of low density lipoproteins and high density lipoproteins.

18 Claims, 14 Drawing Sheets

Specification includes a Sequence Listing.

12% SDS-PGAE gel rPLY gene in pET21a vector (SEQ ID NO:1)

PLY size: 55 kDa rPFO gene in pET28a vector (SEQ ID NO:2)

rLLO gene into pET21a vector (SEQ ID NO:3)

SLO gene in pET21a vector (SEQ ID NO:5)

SLO Size : 52.25 kDa

METHOD OF MEASURING CHOLESTEROL LEVELS BY USING IMMUNOGENIC METHOD

CROSS-REFERENCE TO RELATED APPLICATIONS

The present application is a national stage application of International Patent Application No. PCT/KR2016/000689, filed Jan. 22, 2016, and claims the benefit of Korean Patent Application Nos. 10-2015-0011355, filed Jan. 23, 2015 and 10-2016-0007850, filed Jan. 22, 2016 in the Korean Intellectual Property Office, the disclosure of which are incorporated herein.

STATEMENT OF SEQUENCE LISTING

The Sequence Listing submitted in text format (.txt) filed on Jul. 21, 2017, named "SequenceListing.txt", created on Jul. 17, 2017 (8.51 KB), is incorporated herein by reference.

BACKGROUND OF THE INVENTION

Field of the Invention

The present disclosure relates to measuring the cholesterol level, particularly to measuring the cholesterol level based on immunological methods.

Description of the Related Art

Cholesterols are representative blood lipids. It serves as an energy source in the body just like glucose as well as a main source of hormone such as sex and adrenal cortex hormones. For its proper function in the body, they need to move through the circulation in the blood, which requires carriers called lipoprotein. Lipoproteins binding to the cholesterols are divided into LDL (Low Density Lipoprotein) and HDL (High Density Lipoprotein) according to their densities.

Both LDL cholesterol ("LDL-C") and HDL cholesterol ("HDL-C") are required for normal function of cells. However when their levels are not in an optimal range (HDL: over 60 mg/dl; and LDL: below 130 mg/dl), it may pose a severe heath problem. For example, high levels of LDL-C may generate thrombus, resulting in atherosclerosis which may lead to a heart attack, and are implicated in other problems including high blood pressure, stroke, obesity, diabetes, and the like (William P. et al., Incidence of Coronary Heart Disease and Lipoprotein Cholesterol Levels: The Framingham Study, In JAMA, 1986; MR Law N W, S G Thompson. By how much and how quickly does reduction in serum cholesterol concentration lower risk of ischaemic heart disease, In BMJ, 1994.).

Thus, the cholesterol levels are in a routine checklist of a blood test in clinical settings, and appropriate measures are taken accordingly to lower the cholesterol level.

One of the methods to measure the LDL-C level is based on a method called, Friedewald: LDL-c=TC-[HDL-c+TG/k], k=5). However, this equation to calculate the LDL-C level has been reported to be inaccurate when the triglyceride level is over 400 mg/dL or lipoproteins called chylomicrons are present abundantly in the blood (Martin S S et al., J Am Coll Cardiol. 2013 Aug. 20; 62(8):732-9; Larosa J C. J Am Coll Cardiol. 2013 Aug. 20; 62(8):740-1). Other problems include high cost and time.

Korean Patent Application Publication 2010-0091176 relates to kits and methods to quantify the cholesterol level of small, dense LDL, and discloses a method and a reagent for scavenging any cholesterol in LDL other than the small, dense LDL in the presence of a phospholipase; and measuring the quantity of a cholesterol in a lipoprotein which remains after the previous step.

Therefore there exist needs to develop a more convenient and effective method to measure the concentration at a low cost.

SUMMARY OF THE INVENTION

In the present disclosure, there is provided a method to measure the levels of LDL-C and HDL-C based on CDC (Cholesterol Dependent Cytolysin), which specifically recognizes and binds to cholesterol, and anti-apolipoprotein antibodies, which specifically recognize and bind to specific types of lipoprotein, which method can be advantageously used for rapid and accurate detection of cholesterols.

It is therefore an aspect of the present disclosure to provide a method to measure the cholesterol level in vitro comprising a step of contacting a sample in need of determination of the cholesterol level with a CDC (Cholesterol Dependent Cytolysin) as a cholesterol binding protein by which the cholesterol present on the surface of lipoproteins in the sample and the CDC bind to form a "lipoprotein-CDC" complex (a first complex); a step of contacting the first complex with an anti-apolipoprotein antibody by which a second complex consisting of the "lipoprotein, CDC, and antibody" is formed; and a step of detecting the second complex.

Alternatively, the present disclosure provides a method to measure the cholesterol level in vitro comprising a step of contacting a sample in need of determination of the cholesterol level with an anti-apolipoprotein antibody by which the apolipoprotein present in the lipoproteins in the sample and the antibody bind to form a "lipoprotein-antibody" complex (a third complex); a step of contacting the third complex with a CDC specifically binding to cholesterol by which a fourth complex consisting of the "lipoprotein, antibody, CDC" is formed; and a step of detecting the fourth complex.

In the foregoing methods, various CDCs having affinity to cholesterols from gram positive bacteria may be employed.

Still in the foregoing methods, in addition to CDCs, anti-apolipoprotein antibodies specifically recognizing apolipoproteins present in lipoproteins are used. Anti-apolipoprotein antibodies (e.g., anti-apolipoprotein B-100 antibodies or anti-apolipoprotein A-1 antibodies) from various types and/or origins specifically recognizing LDL-C or HDL-C may be used depending on the type of lipoproteins in which cholesterol to be measured is present.

Still in the foregoing methods, various samples in need of cholesterol measurements include for example, whole blood, plasma or serum.

Still in the foregoing methods, the present methods may be embodied in various kits such as ELISA or rapid kits based on lateral flow assay. In one embodiment, CDCs are fixed onto a solid support and anti-apolipoprotein antibodies are labelled with a detectable material to detect a complex, or anti-polipoprotein antibodies are fixed onto a solid support and CDCs are labelled with a detectable material to detect a complex, without being limited thereto.

In another aspect, there is provided a kit to measure the cholesterol level comprising CDC (Cholesterol Dependent Cytolysin) as a cholesterol binding protein and anti-polipoprotein antibodies (e.g., anti-polipoprotein B-100 antibodies or anti-polipoprotein A-1 antibodies).

In another aspect, there is provided a use of CDC (Cholesterol Dependent Cytolysin) and cholesterol antibodies to measure the level of cholesterol.

Advantageous Effects

The present disclosure discloses a method to measure the concentration of the cholesterol using cholesterol binding proteins called CDC (Cholesterol Dependent Cytolysin) and anti-apolipoprotein antibodies. The present method enables a rapid and simple, simultaneous determination of LDL-C and HDL-C at a low cost and thus is applicable to various fields of art requiring their quantification, replacing the previous methods.

DETAILED DESCRIPTION OF THE EMBODIMENTS

Figure 1:
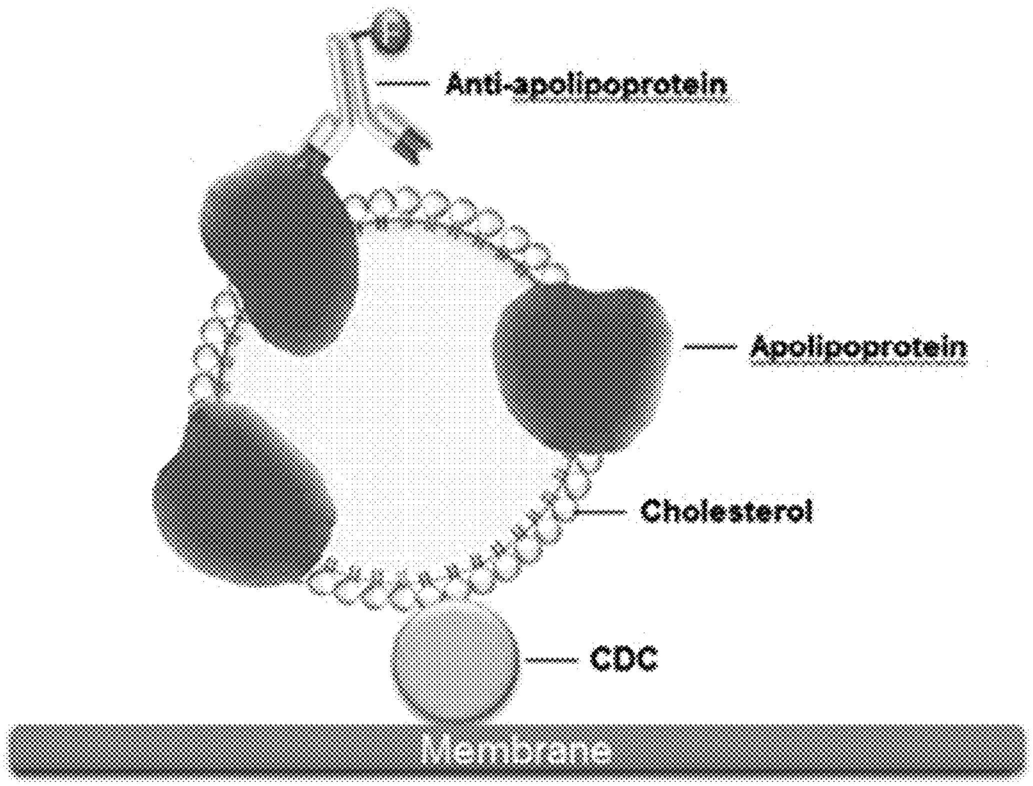
FIG. 1 is a schematic diagram showing one embodiment of the present method using CDCs and anti-apolipoprotein antibodies.
Figure 2:
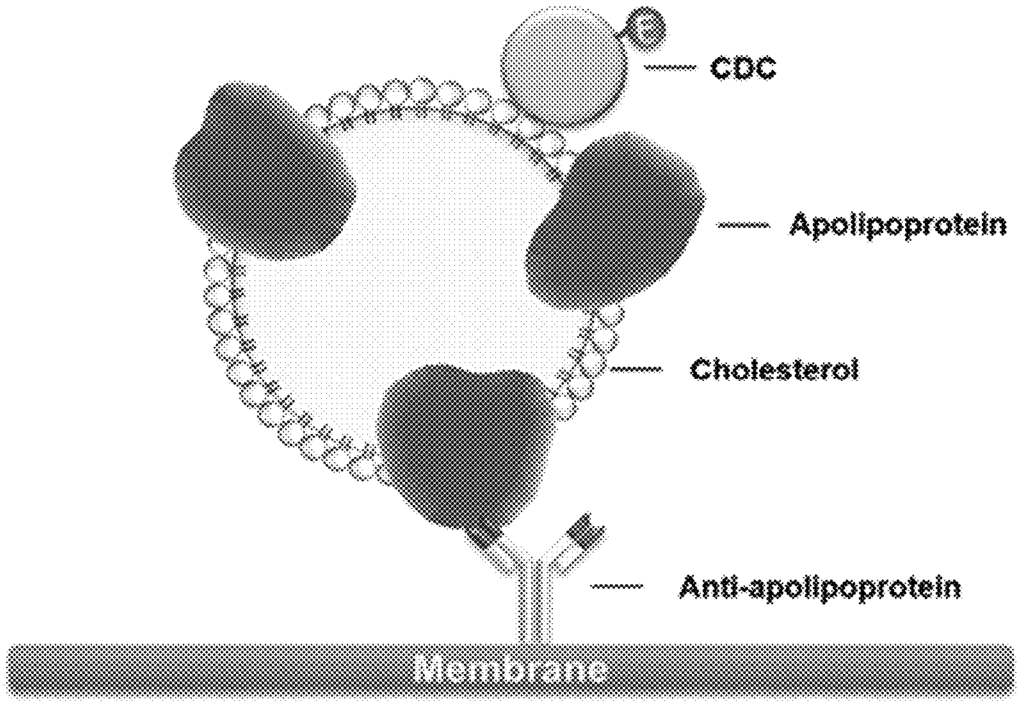
FIG. 2 is a schematic diagram showing another embodiment of the present method using CDCs and anti-apolipoprotein antibodies.

The present disclosure described here is based, in part, on the discovery that the concentration of cholesterol can be determined in a sample by the use of CDC (Cholesterol Dependent Cytolysin) and antibodies against apolipoproteins present in lipoproteins.

The cholesterols that are measured by the present methods are insoluble in an aqueous environment and thus require a carrier protein called lipoprotein to move through the circulation in the blood. The lipoproteins which bind to cholesterol for its movement can be categorized into LDL (Low Density Lipoprotein) and HDL (High Density Lipoprotein). Both LDL-C and HDL-C concentrations need to be measured in clinical settings.

CDCs (Cholesterol Dependent Cytolysin) employed herein belong to a family of toxic proteins that have a beta-barrel form and are secreted from gram positive bacteria. They function in cells by binding to a target cell and inserting themselves having a beta-barrel form into the cell membrane to make a hole through the membrane. It is the cholesterol present on the cell membrane that is required for pore formation. CDCs generally show a strong affinity to cholesterols on the cell membrane.

In the present discourse, methods to determine the concentration of cholesterol in a sample have been developed by unexpected efforts.

In one aspect, the present invention relates to a method of measuring the cholesterol level in vitro comprising: contacting a sample in need of determination of the cholesterol level with a CDC (Cholesterol Dependent Cytolysin) binding to lipoproteins in the sample to form a first complex between "a lipoprotein and the CDC"; contacting the first complex with an anti-apolipoprotein antibody to form a second complex consisting of the "lipoprotein, CDC, and antibody"; and detecting the second complex.

In one aspect of the present invention, by contacting a sample with CDC, cholesterol present on the surface of lipoproteins in the sample and CDC bind to each other, resulting in the formation of a first complex consisting of the lipoprotein and CDC.

In one aspect of the present invention, anti-apolipoprotein antibodies may specifically recognize apolipoproteins present in lipoproteins and may specifically recognize a specific type of lipoproteins. In one aspect of the present invention, an anti-apolipoprotein antibody may be contacted with a first complex and as a result, bind to apolipoproteins present in the first complex, leading to the formation of a second complex consisting of the first complex and the anti-apolipoprotein antibody.

In another aspect, the present invention relates to a method of measuring the cholesterol level in vitro comprising: contacting a sample in need of determination of the cholesterol level with an anti-apolipoprotein antibody specifically recognizing apolipoproteins present in lipoproteins in the sample to form a third complex between "a lipoprotein and the antibody"; contacting the third complex with a CDC (Cholesterol Dependent Cytolysin) as a cholesterol binding protein to form a fourth complex consisting of the "lipoprotein, antibody, and CDC"; and detecting the fourth complex.

In one aspect of the present invention, contacting a sample with an anti-apolipoprotein antibody allows for apolipoproteins present in lipoproteins in the sample and the anti-apolipoprotein antibody to bind to each other, resulting in the formation of a third complex consisting of the lipoprotein and anti-apolipoprotein antibody.

In one aspect of the present invention, contacting the third complex with CDC allows for the cholesterol present on the surface of the lipoproteins contained in the third complex and the CDC to bind to each other, resulting in the formation of a fourth complex consisting of the "lipoprotein, antibody, and CDC."

In one aspect of the present invention, the CDCs which may be employed in the present disclosure include various proteins from gram positive bacteria having affinity to cholesterol. Examples of such may include, but are not limited to, the ones as disclosed below, the sequence of which is known and can be accessed from a public database for example with a number provided in a parenthesis: ALO (Anthrolysin O) from *Bacillus anthracis* (for example UniProt Accession NO: Q81N62); TLO (Thuringiensilysin O) from *B. thurigiensis* (for example NCBI Accession NO: YP_037419); CLO (Cereolysin O) from *B. cereus* (for example NCBI Accession NO: YP_002369889.1); WLO (Weihenstephanensilysin) from *B. weihenstephanensis* (for example NCBI Accession NO: ABY46062), LLO (Listeriolysin O) from *Listeria monocytogenes* (for example NCBI GenBank Accession NO: ABH07645); LSO (Seeligeriolysin O) from *L. seeligeri* (for example Uniprot Accession NO: P31830.1); ILO (Ivanolysin) from *L. ivanovii* (for example NCBI GenBank Accession NO: AAR97343.1); SPH (Sphaericolysin) from *Lysinibacillus sphaericus* (for example NCBI Accession NO: YP_001699692.1); ALV (Alveolysin) from *Paenibacillus alvei* (for example Uniprot Accession NO: P23564); BVL (Brevilysin) from *Brevibacillus brevis* (for example NCBI Accession NO: YP_002770211.1); SLOe (Streptolysin Oe) from *Streptococcus dysgalactiae* (for example NCBI GenBank Accession NO: BAD77791); SLO (Streptolysin O) from *S. pyogenes* (for example NCBI Accession NO: NP_268546.1); SLOc (Streptolysin Oc) from *S. canis* (for example Uniprot Accession NO: Q53957); PSY (Pseudopneumolysin) from *S. pseudonemoniae* (for example NCBI GenBank Accession NO: ACJ76900); PLY (Pneumolysin) from *S. pneumoniae* (for example NCBI GenBank Accession NO: AB021366.1); MLY (Mitilysin) from *S. mitis* (for example NCBI GenBank Accession NO: ABK58695); SLY (Suilysin) from *S. suis* (for example NCBI GenBank Accession NO: ABE66337.1); ILY (Intermedilysin) from *S. intermedius* (for example NCBI GenBank Accession NO: BAE16324.1); LLY (Lectinolysin) from *S. mitis* (for example NCBI GenBank Accession NO: BAE72438.1); PFO (Perfringolysin O) from *Clostridium perfringens* (for example NCBI Accession NO: NP_561079); BRY (Butyriculysin) from *C. butyricum* (for example NCBI Accession NO: ZP_02950902.1); TLY (Tetanolysin O) from *C. tetani* (for example NCBI Accession NO: NP_782466.1); BLYb (Botulinolysin B) from *C. botulinum* B (for example NCBI Accession NO: YP_001886995.1); BLYe (Botulinolysin E3) from *C. botulinum* E3 (for example NCBI Accession NO: YP_001921918.1); BLYc from *C. botulinum* C (Botulinolysin C) (for example NCBI Accession NO: ZP_02620972.1); NVL (Novyilysin) from *C. novyi* (for example NCBI Accession NO: YP_878174.1); VLY (Vaginolysin) from *Gardenella vaginallis* (for example UniProt Accesion NO: B2YGA4), PLO (Pyolysin) from *Arcanobacterium pyogenes* (for example NCBI GenBank Accession NO: AAC45754.1).

In particular, in one aspect of the present invention, the CDC may be LLO (Listeriolysin O), PFO (Perfringolysin O), PLY (Pneumolysin), or SLO (Streptolysin O) or SLO-4 (Domain 4 of Streptolysin O).

CDCs have a characteristic of adhering to the cell membrane and of entering inside of the cells causing a cell lysis by making a pore through the membrane. It is the characteristic of CDCs' binding affinity to cholesterol that is utilized in the present methods. Thus various CDCs exemplified as above in addition to LLO, PFO, PLY, and SLO used herein can also be employed in the present methods.

CDC proteins can be prepared by genetic recombination methods known in the art including for example amplification of a gene of interest followed by expression in bacteria or by methods described in the Examples of the present disclosure.

The present methods can be used for determining the cholesterol level from various samples that require the measurement, which includes for example whole blood, plasma, or serum from mammals, particularly human beings without being limited thereto.

In other exemplary embodiment of the present disclosure, samples which may be employed in the present methods include any samples containing or expected to contain cholesterol, for example whole blood, plasma, or serum without being limited thereto.

In the present methods, the concentrations of each cholesterol can be measured by sequentially reacting a sample, CDC binding to cholesterol present on the surface of lipoproteins in the sample, and an anti-apolipoprotein antibody specifically binding to characteristic apolipoproteins present in lipoproteins in the sample (e.g., antibodies specific to LDL-C or HDL-C).

In a method of measuring the cholesterol level in vitro according to one aspect of the present invention, the concentration of cholesterol (for example, the respective concentrations of LDL-C and HDL-C) can be measured by detecting the second or fourth complex.

In one aspect of the present invention, the detection of a second or a fourth complex may be achieved using various methods known in the art. For example, the concentration may be determined directly by reading the signal generated from a labelling material conjugated to CDC or the anti-apolipoprotein antibody, or indirectly by reading the signal from a separate antibody labelled with chromophores, the separate antibody recognizing CDC or the anti-apolipoprotein antibody.

Methods according to one aspect of the present invention may be embodied by the use of various methods based on immunological reactions.

In one aspect of the present invention, the anti-apolipoprotein antibody may be one or more of an anti-LDL antibody or an anti-HDL antibody, and particularly, may be one or more of an anti-apolipoprotein B-100 antibody or an anti-apolipoprotein A-1 antibody.

In one aspect of the present invention, the anti-apolipoprotein antibody may be two or more distinct antibodies, in which case the antibodies may be distinguishably labelled with different detectable materials.

In one aspect of the present invention, when two or more anti-apolipoprotein antibodies are used, for example, when both an anti-apolipoprotein B-100 antibody and an anti-apolipoprotein A-1 antibody are used, the distinct antibodies may be distinguishably labelled with different detectable materials. Specifically, an anti-apolipoprotein B-100 antibody and an anti-apolipoprotein A-1 antibody, which specifically bind to LDL-C and HDL-C, respectively, can simultaneously detect the levels of both LDL-C and HDL-C in a sample when they are used together while being labelled with different detectable materials.

The antibodies which may be employed in a method according to one aspect of the present invention specifically recognize LDL-C, HDL-C, or Apo proteins contained in the above lipoproteins. For example, in the case of LDL-C, an antibody specific for apolipoprotein B-100 may be used, and in the case of HDL-C, an antibody specific for apolipoprotein A-1. These antibodies are commercially available or may be prepared by methods known in the art. For example, the antibodies of interest may be prepared by the methods disclosed in the present Examples. Also the antibodies which may be used in the present disclosure include monoclonal or polyclonal antibodies. Further the antibodies which may be used in the present disclosure include full length or partial length of antibodies, aptamers, avidity multimers or peptidomimetics.

In one aspect of the present invention, the method according to the present invention may be performed by ELISA or a lateral flow assay.

In one embodiment of the present disclosure, ELISA (enzyme-linked immunosorbent assay) may be used. ELISA is a method to quantify or detect a particular components (antigen) present in minute amount (generally below nanogram) in biological samples. For example, proteins with specific affinity to the component of interest are conjugated to inert polymers and biological samples are applied thereto to form a complex between the component of interest in the sample and the proteins, after which the complex is detected by using a proper antibody. The detection antibodies are conjugated with an enzyme as described hereinafter able to catalyze a reaction in the presence of appropriate substrate to generate a signal such as light or a color change. The signals generated are then detected and the concentrations of the components of interest are determined accordingly.

In this case, CDCs are fixed to a polymer (a solid support) and lipoproteins, the circulating form of cholesterol in the blood, (e.g., LDL-C or HDL-C) are applied thereto to form a complex. The detection uses the complex and an anti-apolipoprotein antibody recognizing a specific type of lipoproteins, which antibody may be labelled. Or additional labelled antibodies recognizing the above antibody may be used.

In another example, an anti-apolipoprotein antibody (e.g., anti-LDL antibody or anti-HDL antibody) may be fixed to an inert polymer support and the biological sample is applied thereto. Then an antibody specific to CDCs binding to the above cholesterol is applied thereto after the unbound sample is removed, and the cholesterol level is measured using the detectable material labeling the CDC.

Specifically, in one aspect of the present invention, one of the CDC and the anti-apolipoprotein antibody may be fixed on a solid support and the other may be labelled with a detectable material. More specifically, in one aspect of the present invention, the CDC is fixed on a solid support and the anti-apolipoprotein antibody is labelled with a detectable material.

In one aspect of the present invention, the CDC or the anti-apolipoprotein antibody may be fixed on a solid support in advance of contacting it with other substances (for example, a sample or complex).

In one aspect of the present invention, the solid support may have an inert surface to which CDCs or anti-apolipoprotein antibodies can be attached, and include but are not limited to, beads, membranes, slides, or microtiter plates, made of glass, plastic (for example polystyrene), polysaccharide, nylon or nitrocellulose.

CDCs or anti-apolipoprotein antibodies in accordance with the present disclosure may be labelled with proper labeling material, which can be detected. The labeling materials refer to materials that can generate signals detectable by proper methods such as spectroscopic, optical, photochemical, biochemical, enzymatic, electrical and/or immunological methods. Such materials include but are not limited to, for example, a fluorescent moiety, a chemiluminescent moiety, a bioluminescence moiety, a magnetic particle, an enzyme, a substrate, a radioisotope and a chromophore.

Specifically, in one aspect of the present invention, CDCs or anti-apolipoprotein antibodies may be labelled with labeling materials enabling direct or indirect detection such as, for example radioisotopes such as $^{3}H$ or $^{125}I$, fluorescent materials, chemiluminescent materials, hapten, biotin, digoxigenin and the like for quantitative or qualitative detection. Or in the present methods, the quantitative or qualitative detection may be performed by using antibodies conjugated with an enzyme such as a horseradish peroxidase, an alkaline phosphatase, or a maleate dehydrogenase, which generates a color change or light upon reaction in the presence of a proper substrate. The quantitative or qualitative determination of the component of interest (e.g., HDL-C or LDL-C) in the sample can then be determined from the amounts of anti-apolipoprotein antibodies or CDCs bound to a detectable material, which is measured by the intensity of the light or color generated. For example, Biochemistry, 2nd edition, B. D. Hames and N. M. Hooper, Springer-Verlag New York 2000, pages 112-114 may be referred for further details.

In one aspect, the present invention may relate to a method of measuring the cholesterol level in vitro, the method comprising: contacting a sample in need of determination of the cholesterol level with an anti-apolipoprotein antibody to form the third complex; contacting the third complex with a CDC (Cholesterol Dependent Cytolysin) as a cholesterol binding protein to form the fourth complex; and detecting the fourth complex using the antibody, wherein the CDC is fixed on a solid support in advance of contacting the sample with the anti-apolipoprotein antibody, the antibody is an anti-apolipoprotein B-100 antibody or an anti-apolipoprotein A-1 antibody, and the antibody is labelled with a detectable material.

In one aspect, the present invention may relate to a kit for measuring the cholesterol level comprising CDC (Cholesterol Dependent Cytolysin) as a cholesterol binding protein and an anti-apolipoprotein antibody.

In one aspect of the present invention, the kit may be a lateral flow assay kit.

The kit according to one aspect of the present invention may be to measure the cholesterol level by the measurement method according to one aspect of the present invention.

In other embodiment of the present disclosure, a rapid kit based on lateral flow assay may be used. In this case, CDC, or LDL or HDL antibodies are attached to the surface of a solid substrate, which for example is provided as glass slides or nitrocellulose membranes. Rapid kits based on lateral flow assay are known in the field of POCT (Point of care test) art, in which CDCs are attached to a solid support such as nitrocellulose membrane and then the reaction mixture of a sample such as serum and an anti-apolipoprotein B-100 antibody or an anti-apolipoprotein A-1 antibody is contacted with the membrane by applying the mixture at one end of the membrane. By such contact, the mixture moves through the membrane by a capillary action during which cholesterols in the sample bind to CDCs fixed to the surface of the solid substrate and the concentration of cholesterols can be determined by detecting the signals generated from the labeling materials conjugated to the anti-apolipoprotein antibodies bound to the apolipoproteins of lipoproteins.

In one aspect, the present invention relates to a lateral flow assay kit for measuring the cholesterol level comprising CDC (Cholesterol Dependent Cytolysin) as a cholesterol binding protein and an anti-apolipoprotein antibody, wherein the CDC is fixed on a solid support, and the antibody is an anti-apolipoprotein B-100 antibody or an anti-apolipoprotein A-1 antibody and is labelled with a detectable material.

The components comprised in the present kits and the methods which may be used with the present kit are as described hereinbefore and the Examples.

The present disclosure is further explained in more detail with reference to the following examples. These examples, however, should not be interpreted as limiting the scope of the present invention in any manner.

EXAMPLES

Materials

Female

BALB/c mice of 6-8 weeks were used. Human HDL and LDL were purchased from ProSpec (USA), complete Freund's adjuvant and Freund's incomplete adjuvant were purchased from MP Biomedicals Inc (USA). Fetal bovine serum (FBS) and Dulbecco's Modified Eagle Medium (4.5 g/L DGlucose, L-Glutamine, 110 mg/L sodium pyruvate), HAT supplement, and HT supplement, Antibiotics were purchased from Gibco (USA). PEG1500 (Polyethylene Glycol 1500) were purchased from Roche (Swiss). The medium contained 10% FBS. Pristane (2,6,10,14-tetrametheylepentadecane) and Protein G Immobilized on agarose were purchased from Sigma (USA).

For isotyping, Pierce™ Rapid Mouse Antibody Isotyping Kits (Quickly determine mouse monoclonal antibody (MAb) class and subclass identity.) were used.

For ELISA, anti-mouse IgG-HRP from KPL (USA) was used as a secondary antibody. TMB/E solution was purchased from EMD Millipore Corporation (USA). Streptavidin-HRP was purchased from R&D systems (USA). The blocking buffer were prepared by adding 1% BDA in 0.1% PBS/T.

For cartridge preparation and fluorescent conjugation, NC membrane HFB13504 from Millipore was used. As a sample pad, Whatman 903 was used. As an absorbent pad, TN415 from Woorichem (Korea). FPR-648 from BioActs (Korea) was used for fluorescent conjugation. DDB contains 1% BSA, 0.1% Tween-20, 0.1% NaN3 in 0.1% PBST pH 7.4. DB was prepared by adding 1 μg/ml anti-LDL #4c2, and 50 ng/ml anti-DNP #3A6G9 to DDB.

Example 1. Preparation of HDL and LDL Antibodies 1-1. Immunization

To induce an immunization reaction in mice, the LDLs were intraperitoneally (I.P.) injected into the mice. For a first immunization, 200 μg/200 μl of human LDL and HDL were mixed with 100 μl of complete Freund's adjuvant, and the mixture were intraperitoneally injected into BALB/c mice at 300 μl/mouse. After 10 days of the first injection, the mixture of HDL, LDL and Freund's incomplete adjuvant was injected every 10 days for a total of 3-4 times. For a cell fusion, 500 μg/300 μl of HDL and LDL without the adjuvant was intraperitoneally injected.

1-2. Feeder Cell Preparation

One day before fusing cells, BALB/c mice of 7-8 weeks of age were sacrificed under $CO_2$ and the coat was removed. Then 5 ml of 11.6% sucrose solution was intraperitoneally injected and the site of injection was massaged for 1 min. Then the sucrose solution with macrophage were recovered from the peritoneal cavity using syringe, which were transferred to a tube and centrifuged at 1500 rpm for 1 min to collect feeder cells. The feeder cells were then suspended in HAT complete DMEM and seeded onto each well of five 96 well plates at 140 μl/well and incubated overnight at 37° C. $CO_2$ incubator.

1-3. Cell Fusion

This example describes a process to prepare B cells, an immune cell. The spleen was removed from the mice immunized with HDL and LDL. The spleen was then placed onto a culture dish containing incomplete DMEM and dissected into smaller pieces, which was then transferred to a tube and precipitated for 5 min to collect the supernatant.

Then SP2/O cells were used as myeloid cells, which were cultured in 75T $cm^2$ flask until at least 75% confluency. The cells were then centrifuged at 1500 rpm for 5 min for precipitation. The precipitated cells were then mixed with B cells and centrifuged at 1500 rpm for 1 min. The precipitated mixture of cells were then dispersed and 1 ml of PEG1500 (Polyethylene Glycol 1500) was added thereto in small portions for 90 seconds while shaking the tube for improving the fusion. Then the tube was shaken again for an additional 90 seconds and complete DMEM (40 ml) was added slowly for 10 min, which was then centrifuged for 1 min at 1500 rpm. The precipitated cells were then suspended in HAT complete DMEM and seeded onto a plate with feeder cells at 140 μl/well and incubated in a 37° C. $CO_2$ incubator.

1-4. Screening

For a first screening, when the colonies were formed after the cell fusion, the medium was removed and 280 μl/well of fresh HAT complete DMEM was added. When the colonies were grown big enough, indirect ELISA was used for screening. 1 μg/ml of HDL, LDL was added at 50 μl/well and incubated for 2 hours at 37° C. Then each well was washed with 1×PBST 3 times and then blocking buffer was added to each well at 200 μl/well followed by an incubation at 37° C. for 1 hour. Then the wells were washed with 0.1% PBST 3 times and 50 μl/well of medium with fused cells was added as a first antibody and incubated at 37° C. for 1 hour. Then the wells were washed with 0.1% PBST for 3 times and as a second antibody 200 ng/ml of anti-goat mouse IgG HRP was added at 50 μl/well and incubated at 37° C. for 1 hour. Then the wells were washed with 0.1% PBST 3 times and 100 μl/well of TMB/E solution was added to each well and incubated for 15 min at RT. Then the absorbance of each well was measured at 630 nm using ELISA reader and only the wells having absorbance of 1.0 and above were selected for further screening. The cells from the selected wells were then transferred to each well of 24 well plate and cultured in HAT complete DMEM in 37° C. $CO_2$ incubator. The cells were monitored and a second screening was performed as described in the first screening when the cells were fully grown. The cells of a well having O.D. value of 1 or above at 650 nm were transferred to each well of 6 well plate. By this way, 3rd and 4th screenings were performed and the screened cells were transferred to 75T $cm^2$ flask. The cells were sub-cultured and the parent cells were stored frozen.

1-5. Cloning and Subculture

Homogenous clones of the cells producing antibody were isolated through cloning process as described below. As a first step, the feeder cells were seeded onto each well of 96 well plate and incubated overnight in a 37° C., $CO_2$ incubator. Next the parent cells were counted and diluted to include one cell in 140 μl, which was added to each well and incubated in a 37° C., $CO_2$ incubator to obtain a colony. Then indirect ELISA was used to select monoclonal cells with higher value and successively subcultured from 96 well, to 24 well, to 6 well plate, to 25 $cm^2$ T flask and finally to 75 $cm^2$ T flask.

1-6. Mouse Experiment

BALB/C was injected with pristine at 300 μl/mouse to disable the immune system. After 7 days, the fused cells were diluted in incomplete DMEM at the concentration of 1×10^6, which were then intraperitoneally injected into mice at 300 μl/mouse. The ascites fluid generated after the injection was harvested with a syringe from the mice anesthetized with $CO_2$ inhalation. The ascite harvested then was centrifuged at 3500 rpm for 15 min to remove tissues and lipids and the like and to collect the supernatant, which was stored frozen at −20° C. until use.

1-7. Purification of Monoclonal Antibodies and Confirmation

The frozen ascite prepared above was melted at RT and centrifuged at 12000 rpm for 40 min to remove any residual lipids. Then 55% ammonium sulfate was added to the supernatant and dissolved, which were incubated overnight at 4° C. and centrifuged at 15000 rpm for 40 min to collect precipitates. The precipitates were dissolved in the same volume of 1×PBS (pH 7.4) as that of the ascite and desalted by dialysis. For dialysis, 1×PBS pH 7.4 was used as a buffer and the buffer was changed every 3 hours for a total of 4 times. The dialyzed ascite was diluted 5 times with 1×PBS pH 7.4 and applied to a column filled with protein-G to which the proteins are binding. The unbound proteins were removed by washing the column with 1×PBS pH 7.4. Then 100 mM glycine buffer pH 2.5 was applied to the column for elution in 3 ml aliquots. 1M Tris-Cl pH 8.0 was used as a neutralization buffer.

Figure 3A:
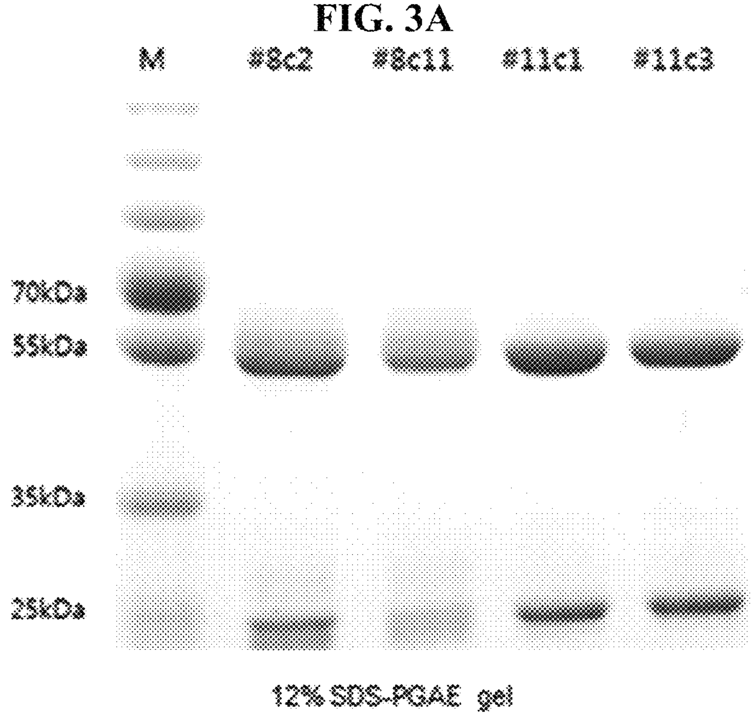
FIG. 3A is a result of SDS-PAGE of the antibody to anti-HDL prepared in one embodiment of the present disclosure.
Figure 3B:
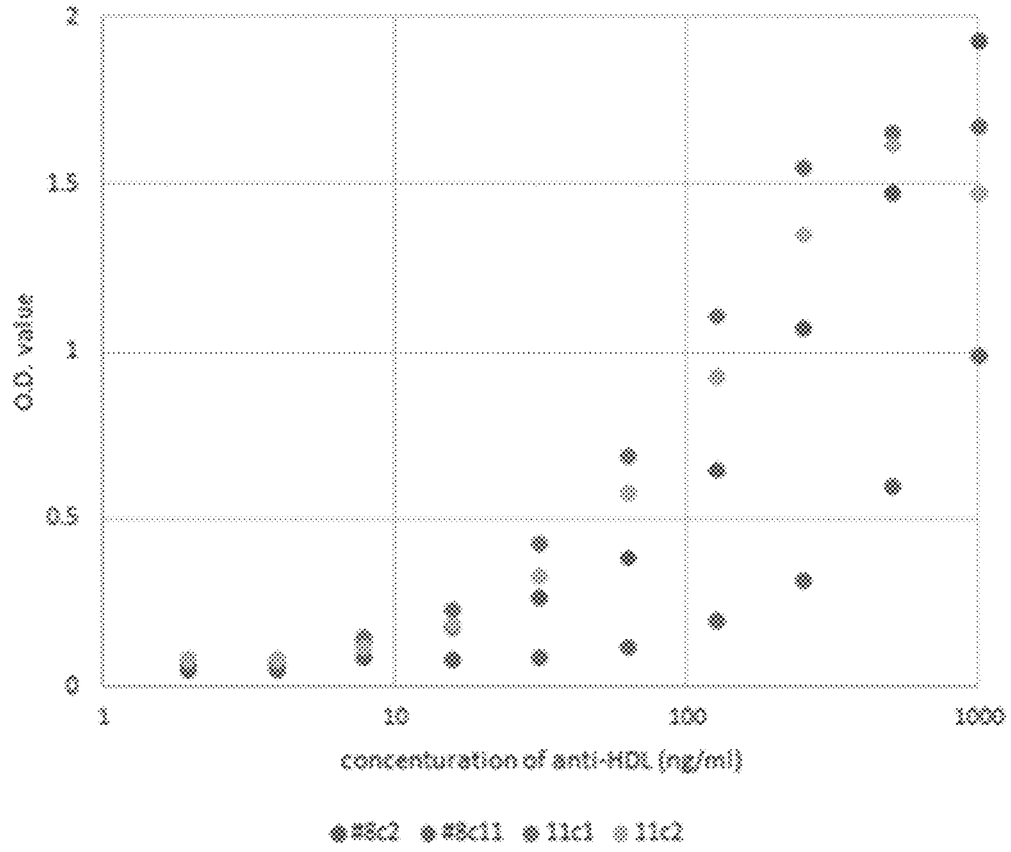
FIG. 3B is a result of ELISA measuring the activity of anti-HDL antibodies identified in FIG. 3A against HDL-C according to their concentration.
Figure 4A:
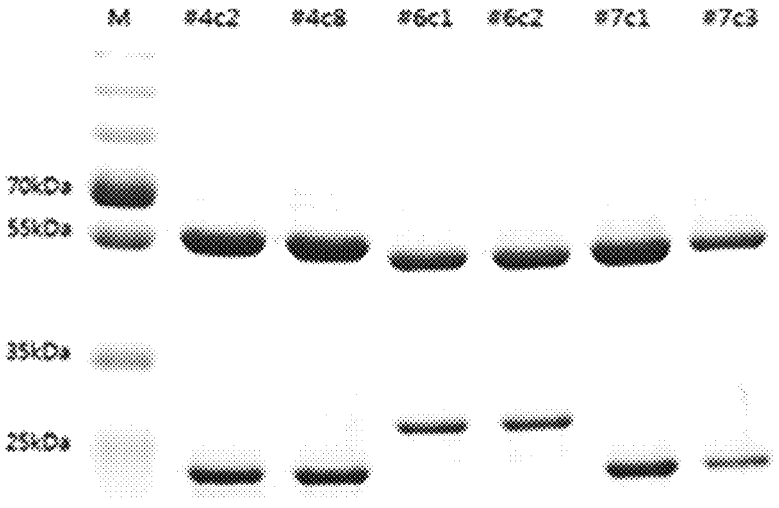
FIG. 4A is a result of SDS-PAGE of the antibody to LDL prepared in one embodiment of the present disclosure.
Figure 4B:
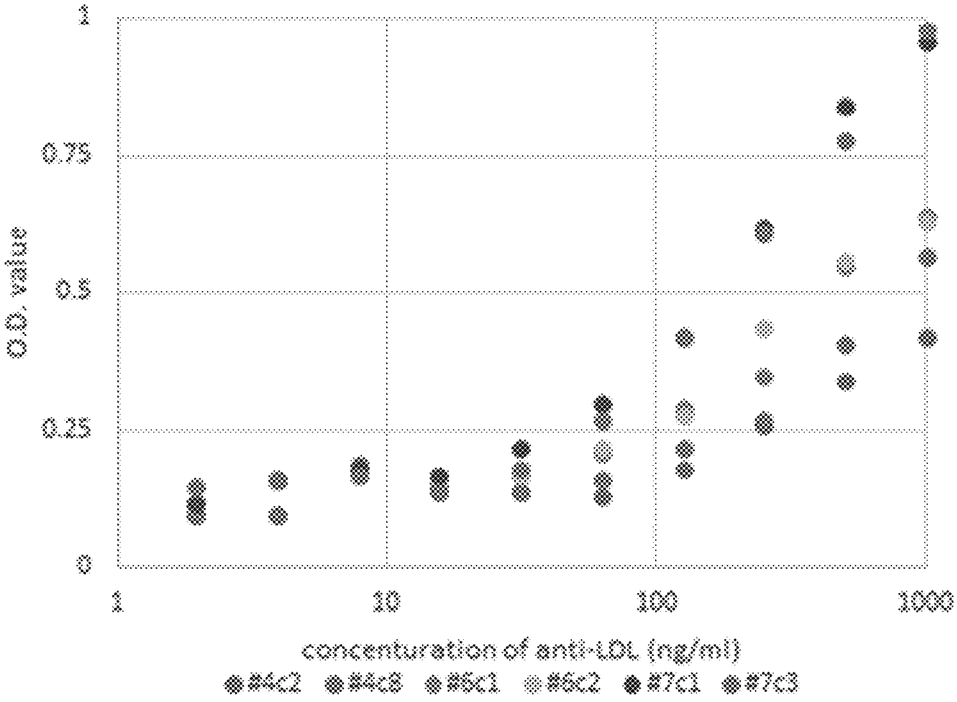
FIG. 4B is a result of ELISA measuring the activity of anti-LDL antibodies identified in FIG. 4A against HDL-C according to their concentration.

To remove glycine, a dialysis in 1×PBS pH 7.4 was performed. The purified antibody was confirmed to consist of a heavy chain 50-55 kDa and a light chain 20-25 kDa in size in a SDS-PAGE gel, which was then used for ELISA. To each well of 96 well plate, HDL, LDL of 1 μg/ml was added at 50 μl/well and the plate was incubated at 37° C. for 2 hours followed by washing 3 times with 0.1% PBST and blocked for 1 hour in 200 μl/well of blocking buffer at 37° C. Then the plate was washed 3 times with 0.1% PBST and incubated with 50 μl/well of the 1st antibody prepared by two-fold serial dilution starting from 1 μg/ml at 37° C. for 1 hour. Then the plate was washed 3 times with 0.1% PBST and incubated with 50 μl/well of anti-goat mouse IgG HRP of 200 ng/ml as a second antibody at 37° C. for 1 hour. Then the plate was washed 3 times with 1×PBST and incubated with 100 μl/well of TMB/E for 15 min at RT followed by reading at O.D. 650 nm using an ELISA Reader. Results are shown in FIGS. 3 and 4, which confirm that the purified antibodies of the present disclosure have both a light and a heavy chain and specifically recognize each corresponding antigen.

Example 2. Preparation of CDC (Cholesterol Dependent Cytolysin)

2-1. Preparation of Pneumolysin (PLY)

Pneumolysin (PLY) is a protein produced from *Streptococcus pneumoniae* and has an amino acid sequence appropriate for production of recombinant PLY (NCBI ID: WP_001284361.1), which was used for codon optimization to generate an optimized nucleotide sequence encoding the same. The polynucleotide having an optimized codon sequence was then synthesized from Bioneer (Korea).

The gene was then amplified by PCR and cloned into BamHI/XhoI site of pET21a (Novagen), which was then transformed into a host cell BL-21™ DE3 Star to select a clone expressing rPLY. pET-21a.ply_BL21™ DE3 star cells were grown in O/N and subcultured in 4.2 L LB medium containing Amp+ cam at 37° C. with shaking at 200 rpm. When O.D value has reached 0.5, the culture was induced at 30° C. for 4 hours in the presence of IPTG at the final concentration of 20 mM. Then the cells were harvested. The cells were then resuspended in 150 ml of native purification buffer containing protease, DNase and RNase. Then cells were lysed by sonication 10 times under 10 sec sonication and 10 sec rest cycle at 80% amplitude. The cell lysates were centrifuged for 30 min at 10000 rpm. 10 ml of 50% TALON resin (Clonetech) was applied to a purification column of 20 ml in size. The resins were completely stabilized (5-10 min) and eluted. 40 ml of sterilized water was used to resuspend the resin by tapping the column in upside down position. Then 10 ml of Native purification Buffer (50 mM NaH2PO4, pH 8.0; 0.5 M NaCl) was used to resuspend the resin by tapping the column in upside down position. After stabilizing the resin, the supernatants were decanted. The process was repeated one more time.

150 ml of lysates were prepared in a native condition and replaced with 10 mM imidazole. The lysate was then mixed with the prepared resin on a roller mixer for 1 hour. The resin was then transferred to the column and stabilized. The flow obtained was again transferred to the stabilized column and the fractions were collected.

Figure 5:
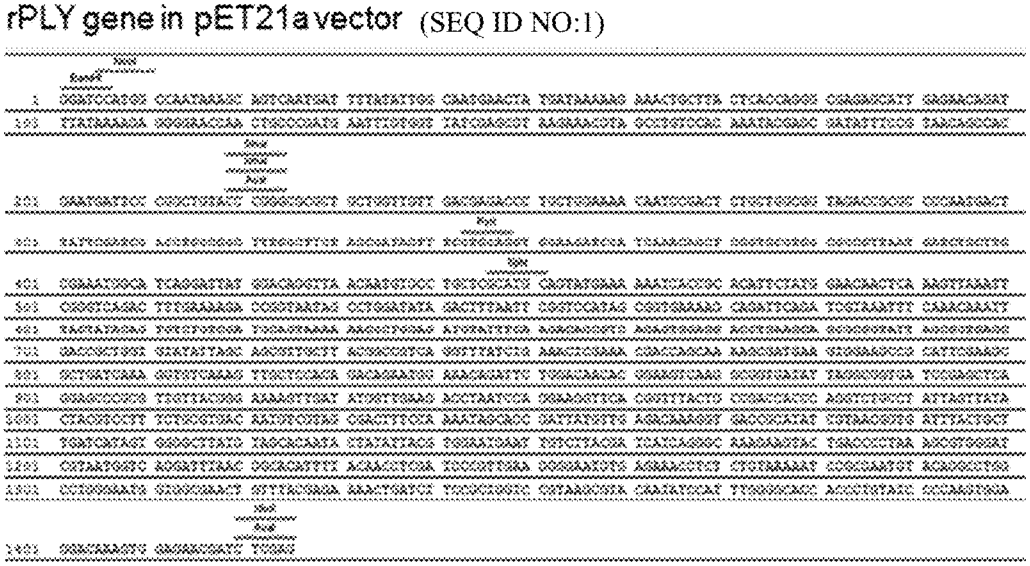
FIG. 5 shows a nucleic acid sequence of a PLY (SEQ ID NO:1) prepared in the present disclosure as one example of CDC and a result of SDS-PAGE of a purified recombinant PLY expressed and isolated in one embodiment of the present disclosure.
Figure 5:
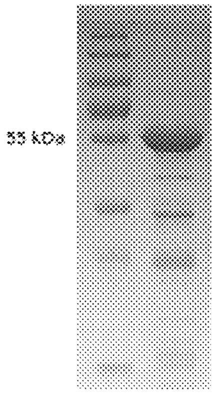

30 ml Native Wash Buffer (50 Mm NaH2PO4, pH 8.0; 0.5 M NaCl, 20 mM imidazole) was applied to the column and eluted 5 times. For a SDS-PAGE analysis, the supernatant was stored at 4° C. The column was eluted with 20 ml of Native Elution Buffer (50 mM NaH2PO4, pH 8.0; 0.5 M NaCl, 250 mM imidazole) and subjected to a filtration using centricon ultra-filtration (10,000 MWCO) exchanged with PBS (G+E, pH 7.4). As shown in FIG. 5, recombinant Pneumolysin was successfully expressed, and purified under a native condition.

2-2. Preparation of Perfringolysin O (PFO)

Perfringolysin O (PFO) is a protein produced from *Clostridium perfringens* and has an amino acid sequence appropriate for production of recombinant PFO (NCBI ID: WP_003467630.1), which was used for codon optimization to generate an optimized nucleotide sequence encoding the same. The polynucleotide having an codon optimized sequence was then synthesized from Bioneer (Korea).

The gene was then amplified by PCR and cloned into a BamHI/XhoI of pET21a (Novagen), which was then transformed into a host cell BL-21™ DE3 Star to select a clone expressing rPFO. pET-21a.pfo_BL-21 DE3 star cells were grown in O/N and subcultured in 5.4 L LB medium containing Kan+ cam at 37° C. with shaking at 200 rpm. When the O.D value has reached 0.5, the culture was induced at 30° C. for 4 hours in the presence of IPTG at the final concentration of 0.2 mM. Then the cells were harvested. The cells were then resuspended in 150 ml of native purification buffer containing protease, DNase and RNase. Then cells were lysed by sonication 10 times under 10 sec sonication and 10 sec rest cycle at 80% amplitude. The cell lysates were centrifuged for 30 min at 10000 rpm. 10 ml of 50% TALON resin (Clonetech) was applied to a purification column of 20 ml in size. The resins were completely stabilized (5-10 min) and eluted. 40 ml of sterilized water was used to resuspend the resin by tapping the column in upside down position. The resin was stabilized before the supernatant was decanted. Then 10 ml of native purification Buffer (50 mM NaH2PO4, pH 8.0; 0.5 M NaCl) was used to resuspend the resin by tapping the column in upside down position. After stabilizing the resin, the supernatants were decanted. The process was repeated one more time.

Figure 6:
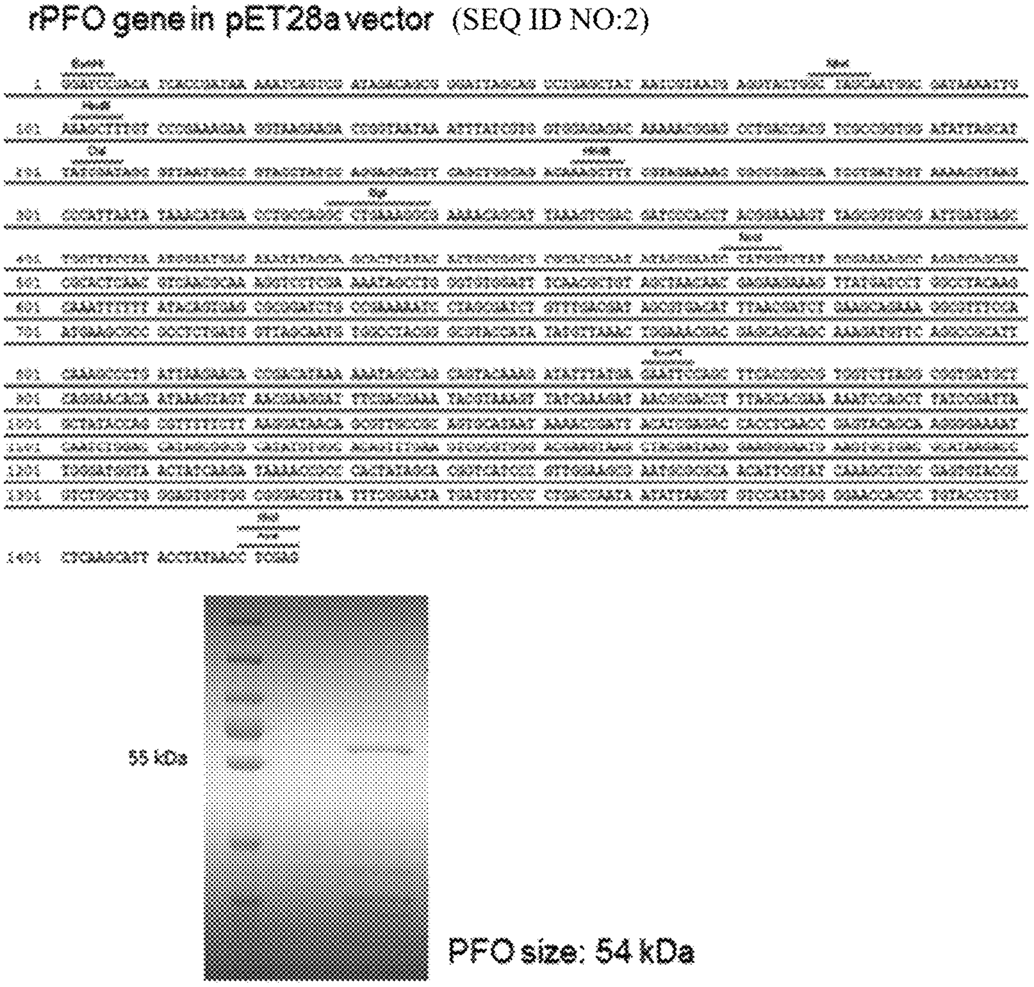
FIG. 6 shows a nucleic acid sequence of a PFO (SEQ ID NO:2) prepared in the present disclosure as one example of CDC and a result of SDS-PAGE of a purified recombinant PFO expressed and isolated in one embodiment of the present disclosure.

150 ml of the lysates were prepared in a native condition and replaced with 10 mM imidazole. The lysate was then mixed with the prepared resin on a roller mixer for 1 hour. The resin was then transferred to the column and stabilized. The flow obtained was again transferred to the stabilized column and the fractions were collected. 30 ml Native Wash Buffer (50 Mm NaH2PO4, pH 8.0; 0.5 M NaCl, 20 mM imidazole) was applied to the column and eluted 5 times. For a SDS-PAGE analysis, the supernatant was stored at 4° C. The column was eluted with 20 ml of Native Elution Buffer (50 mM NaH2PO4, pH 8.0; 0.5 M NaCl, 250 mM imidazole) and subjected to a filtration using centricon ultra-filtration (10,000 MWCO) exchanged with PBS (G+E, pH 7.4). As shown in FIG. 6, recombinant Perfringolysin O was successfully expressed, and purified under a native condition.

2-3. Purification of Listeriolysin O (LLO)

Listeriolysin O (LLO) is a protein produced from *Listeria monocytogenes* and has an amino acid sequence appropriate for production of recombinant LLO (NCBI ID: WP_003722731.1), which was used for codon optimization to generate an optimized nucleotide sequence encoding the same. The polynucleotide having an codon optimized sequence was then synthesized from Bioneer (Korea).

Figure 7:
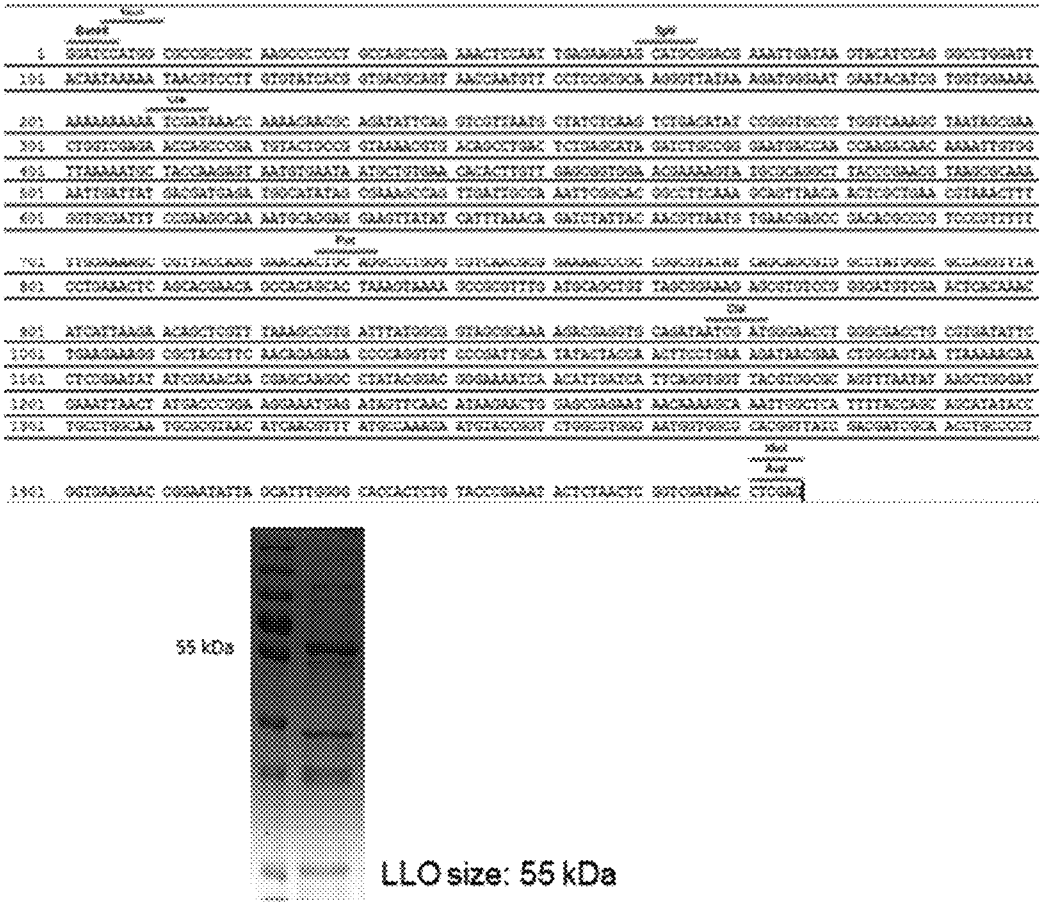
FIG. 7 shows a nucleic acid sequence of a LLO (SEQ ID NO:3) prepared in the present disclosure as one example of CDC and a result of SDS-PAGE of a purified recombinant LLO expressed and isolated in one embodiment of the present disclosure.

The gene was then amplified by PCR and cloned into a BamHI/XhoI of pET21a (Novagen) as shown in upper portion of FIG. 7, which was then transformed into a host cell Codon plus (RIPL) to select a clone expressing rLLO. pET-21a.LLO_Codon Plus(RIPL) cells were grown in O/N and subcultured in 5.4 L LB medium containing Amp+ cam at 37° C. with shaking at 200 rpm. When the O.D of the cells has reached 0.5, the culture was induced at 18° C. with 0.2 mM IPTG. Then the cells were harvested. The cells were then resuspended in 150 ml of native purification buffer containing protease, DNase and RNase. Then cells were lysed by sonication 10 times under 10 sec sonication and 10 sec rest cycle at 80% amplitude. The cell lysates were centrifuged for 30 min at 12000 rpm. 5 ml of 50% TALON resin (Clonetech) was applied to a purification column of 20 ml in size. The resins were completely stabilized (5-10 min) and eluted. 10 ml of sterilized water was used to resuspend the resin by tapping the column in upside down position. The resin was stabilized before the supernatant was decanted. Then 5 ml of native purification Buffer (50 mM $NaH_2PO_4$, pH 8.0; 0.5 M NaCl) was used to resuspend the resin by tapping the column in upside down position. After stabilizing the resin, the supernatant was decanted. The process was repeated one more time.

20 ml of the lysates were mixed with the resin prepared in a native condition on a roller mixer for 1 hour. The resin was then transferred to the column and stabilized. The flow obtained was again transferred to the stabilized resin and the fractions were collected. 15 ml Native Wash Buffer (50 Mm $NaH_2PO_4$, pH 8.0; 0.5 M NaCl, 20 mM imidazole) was applied to the column and eluted 5 times. For a SDS-PAGE analysis, the supernatant was stored at 4° C. The column was eluted with 10 ml of Native Elution Buffer (50 mM $NaH_2PO_4$, pH 8.0; 0.5 M NaCl, 250 mM imidazole) and subjected to a filtration using centricon ultra-filtration (10,000 MWCO) exchanged with PBS (G+E, pH 7.4). As shown in FIG. 7, recombinant Listeriolysin O (LLO) was successfully expressed, and purified under a native condition. The yield was appropriate for the protocol described above to be used in a production of LLO in large scale.

2-4. Expression and Purification of SLO D4

SLO consists of 4 domains and the domain 4 at N-terminus contains SH— group that binds to cholesterol. Thus, domain 4 of SLO was selected and prepared as a recombinant protein in consideration of the 3D structure of SLO, in which SH— group may not be exposed.

The nucleotide sequence encoding the domain 4 was codon optimized and synthesized by GeneArt® (Invitrogen) and cloned into pET100. The cloned vector was then transformed into a host cell *E. coli*, BL-21 Star to select a clone expressing rSLO D4.

pET100.SLO D4-BL-21 star cells were grown in O/N and subcultured in 4.2 L LB medium containing Amp+ cam at 37° C. with shaking at 200 rpm. When the O.D of the cells has reached 0.5, the culture was induced at 30° C. for 4 hours in the presence of 0.2 mM IPTG. Then the cells were harvested. The cells were then resuspended in 150 ml of native purification buffer containing protease, DNase and RNase and were harvested. Then cells were lysed by sonication 10 times under 10 sec sonication and 10 sec rest cycle at 80% amplitude. The cell lysates were centrifuged for 30 min at 10000 rpm. 10 ml of 50% TALON resin (Clonetech) was applied to a purification column of 20 ml in size by pipetting. The resins were completely stabilized (5-10 min) and eluted. 100 ml of sterilized deionized water was used to resuspend the resin by tapping the column in upside down position. The resin was stabilized before the supernatant was decanted. Then 10 ml of native purification buffer (50 mM $NaH_2PO_4$, pH 8.0; 0.5 M NaCl) was used to resuspend the resin by tapping the column in upside down position. After stabilizing the resin, the supernatant was decanted. The process was repeated one more time.

150 ml of the lysates were prepared in a native condition and replaced with imidazole. Then the lysates were mixed with the prepared resin on a roller mixer for 1 hour. The resin was then transferred to the column and stabilized. The flow obtained was again transferred to the stabilized resin and the fractions were collected. 40 ml Native Wash Buffer (50 Mm $NaH_2PO_4$, pH 8.0; 0.5 M NaCl, 20 mM imidazole) was applied to the column and eluted 5 times. For a SDS-PAGE analysis, the supernatant was stored at 4° C. The column was eluted with 20 ml of Native Elution Buffer (50 mM $NaH_2PO_4$, pH 8.0; 0.5 M NaCl, 250 mM imidazole) and subjected to a filtration using centricon ultra-filtration (5,000

Figure 8:
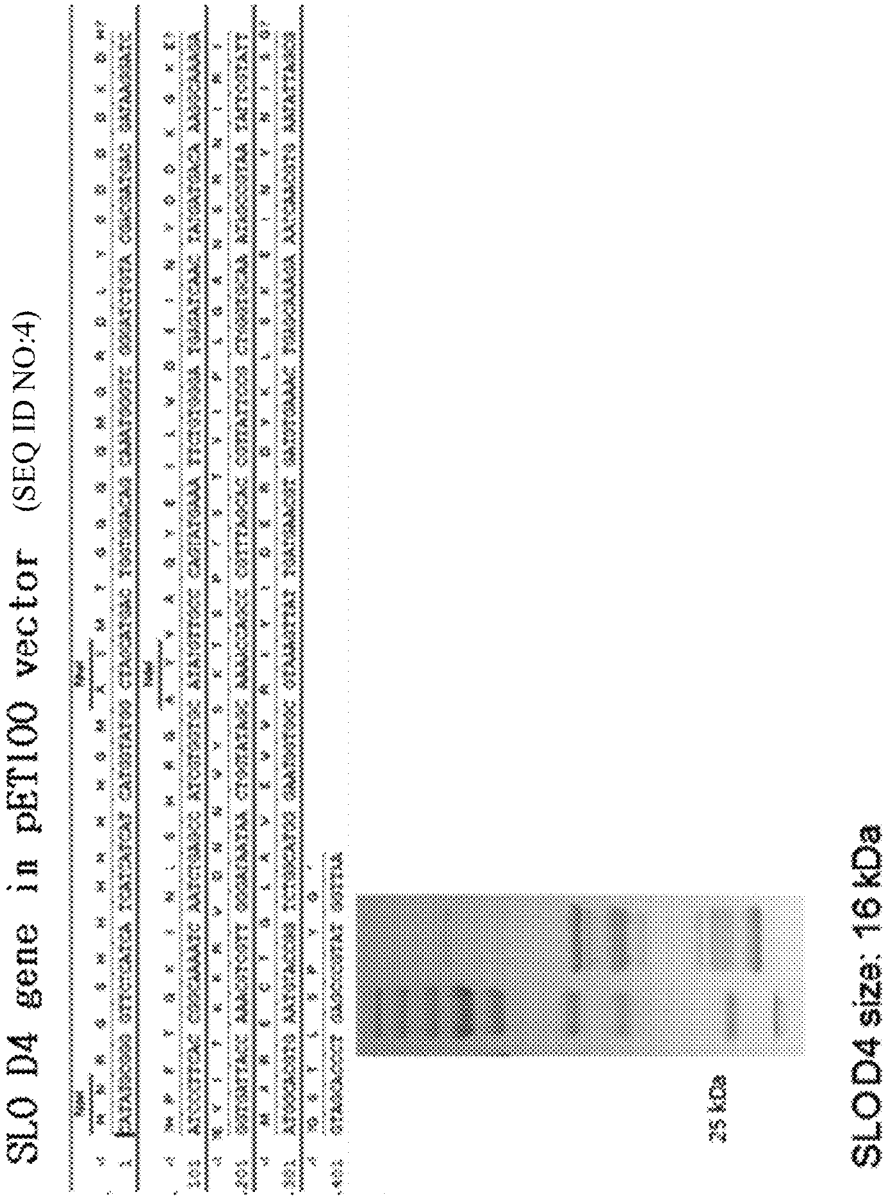
FIG. 8 shows a nucleic acid sequence of a SLO_D4 (SEQ ID NO:4) prepared in the present disclosure as one example of CDC and a result of SDS-PAGE of a purified recombinant SLO_D4 expressed and isolated in one embodiment of the present disclosure.

MWCO) exchanged with PBS (G+E, pH 7.4). As shown in FIG. 8, recombinant SLO D4 was successfully expressed, and purified under a native condition.

2-5. Expression and Purification of SLO

Figure 9:
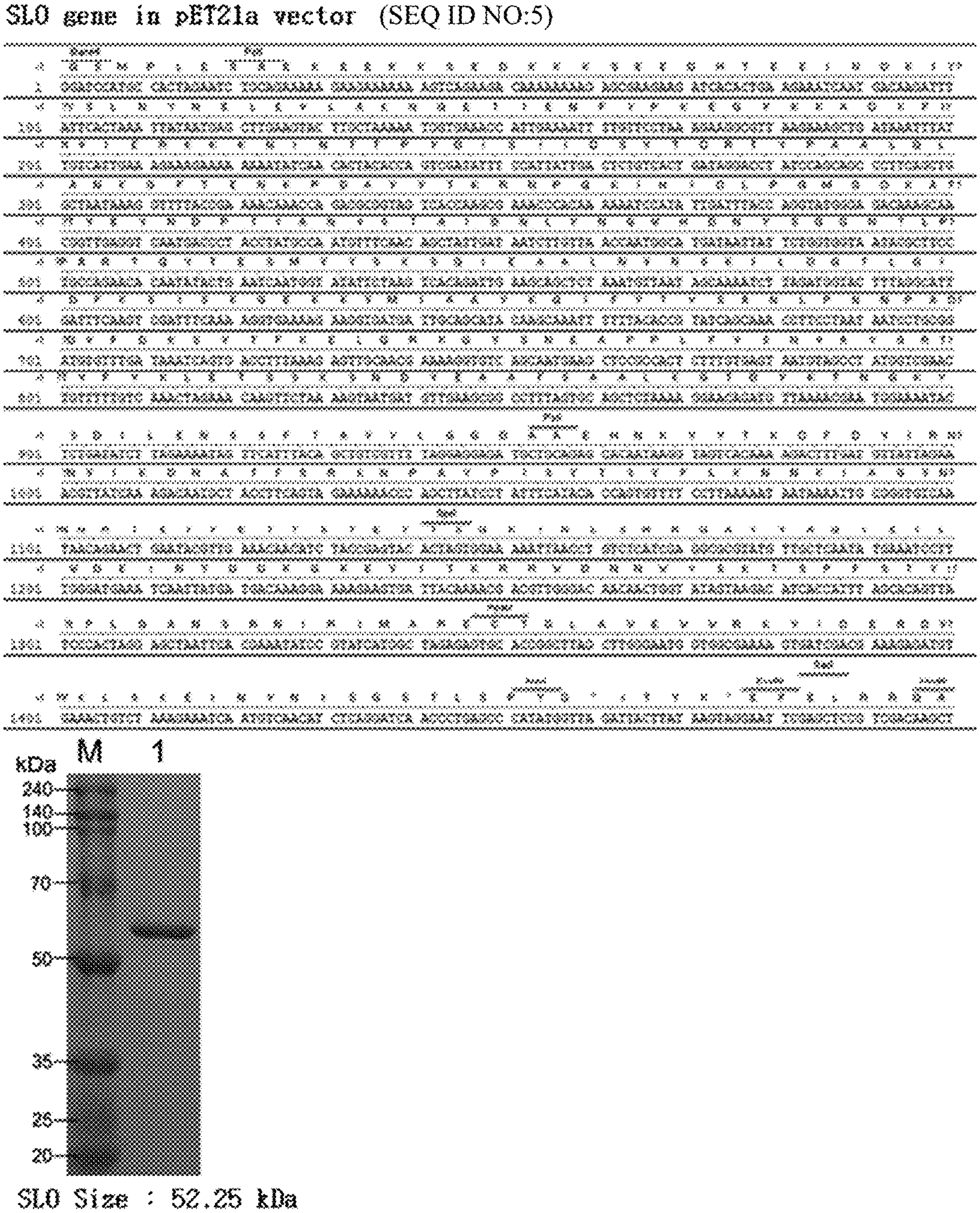
FIG. 9 shows a nucleic acid sequence of a SLO (SEQ ID NO:5) prepared in the present disclosure as one example of CDC and a result of SDS-PAGE of a purified recombinant SLO expressed and isolated in one embodiment of the present disclosure.

As shown in FIG. 9, a gene encoding SLO recombinant protein was amplified by PCR and the PCR product was cloned into pET21a vector, which was used to transform *E. coli*. The cells were then grown in LB medium at 37° C. with shaking at 250 rpm. When the O.D. of the cells has reached 0.5-0.7, IPTG was added to the culture at the final concentration of 1 mM and induced for 3 hours. Then cells were harvested by centrifuge and the pellets were lysed in lysis buffer (10 mM sodium phosphate, 0.5M NaCl, 10 mM 2-mercaptoethanol, 10 mM EDTA, pH 7.0 with NaOH) in the presen of protease inhibitor using a supersonic device (SONICS and MATERIALS INC, USA). Then the expression was confirmed by SDS-PAGE gel analysis. The proteins were purified by exchange chromatography method. Results are shown in FIG. 9.

2-6. Labelling of SLO D4 Protein

Protein and biotin were mixed at the concentration ratio of 10:1 (100 μl) and 1M sodium bicarbonate was added to the mixture at 1/10 of the total voume (10 μl), which was then incubated overnight at 4° C. To pack 1 m of DEAE Sephadex™G-25, resins were placed in a column and centrifuged at 3000 rpm for 20 min to remove buffer. Then biotinylated SLO was put into the column and centrifuged at 2000 rpm for 20 min.

ELISA was performed to confirm the biotinylation of rSLO. SLO-biotin was prepared by two-fold serial dilution starting from 2 μg/ml and added to each well of 8 well strip at 5 μl/well. The wells were then incubated at 37° C. for 2 hours and washed 3 times with 1×PBST followed by blocking with 200 μl/well of 1× blocking buffer at 37° C. for 1 hour. Then the wells were washed 3 times with 1×PBST and were incubated with 50 μl/well of antibody streptavidin-HRP diluted 1/200 at 37° C. for 1 hour. Then the wells were washed 3 times with 1×PBST and incubated with 50 μl/well of TMB/E solution for 15 min. Then the reaction result was analyzed by measuring optical density at 630 nm using an ELISA reader to confirm the biotinylation.

Example 3. Measurement of Cholesterol Concentration by Immunological Method 3-1. Measurement of Cholesterol Using ELISA The antibodies prepared in Example 1 and CDC proteins prepared in Example 2 were used to determine the concentration of cholesterol. Each of CDC proteins was allowed to bind cholesterol present on the surface of lipoproteins and anti-HDL-C antibody (#11C1) or anti-LDL-C antibody (#4C2) was used to detect HDL-C and LDL-C, respectively.

Specifically, 50 μl/well of SLO, SLO_D4, PLY, PFO, LLO at the concentration of 1 μg/'ml prepared in Example 2 was added to each well of 8 well ELISA strip and incubated at 37° C. for 2 hours. Then the strip was washed 3 times with 0.1% PBST and 200 μl/well of blocking buffer was added to each well followed by incubation at 37° C. for 1 hour. Then the strip was washed 3 times with PBST and incubated with HDL or LDL which was serially diluted from 2 μg/ml to 2 ng/ml at 37° C. for 1 hour. Then the strip was washed 3 times with 0.1% PBST and incubated with 50 μl/well of antibody at the concentration of 1 μg/ml prepared in Example at 37° C. for 1 hour. Then the strip was washed 3 times with 0.1% PBST and incubated with 50 μl/well of anti-goat mouse IgG HRP as a secondary antibody diluted 200 ng/ml at 37° C. for 1 hour. Then the strip was washed 3 times with 0.1% PBST and incubated with 100 μl/well of TMB/E solution for 15 min at RT. Then the reaction result was analyzed by measuring optical density at 650 nm using an ELISA reader. Results are shown in FIG. 10 and FIG. 11.

Figure 10:
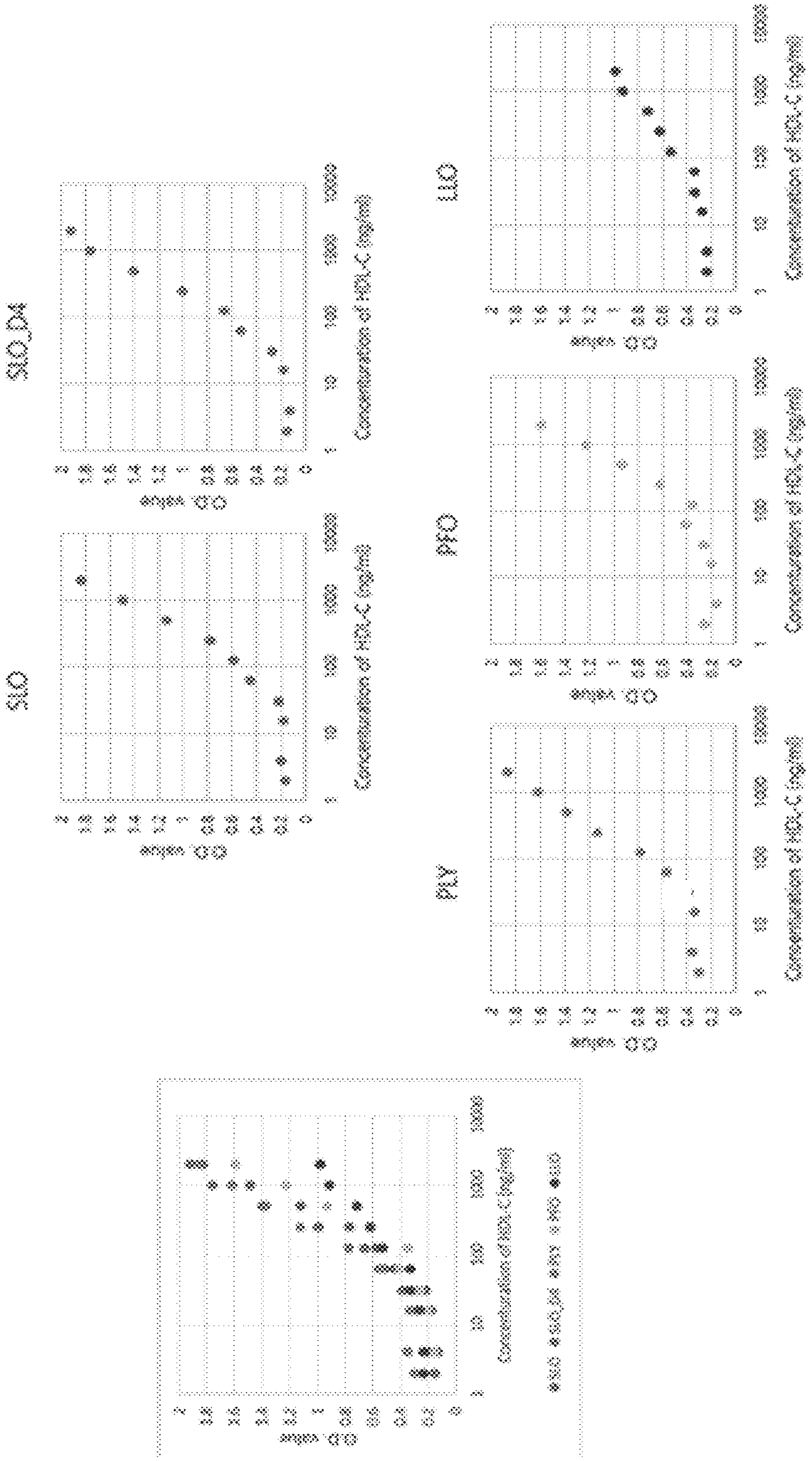
FIG. 10 is a result of measuring the concentration of HDL-C in which cholesterols were bound with CDC (SLO, SLO_D4, LLO, PFO, or PLY) and detected using the antibody #11C1 which recognizes Apo A-1, a main component of HDL-C.

FIG. 10 shows the result of HDL-C concentration measured in which cholesterols present on the surface of lipoproteins were bound to CDC (SLO, SLO_D4, LLO, PFO, PLY) and detected using an antibody #11C1 which recognizes Apo A-1, the main component of HDL-C. This indicates that CDCs when used as a capture are able to detect HDL-C level in a concentration dependent manner upto 30 ng/ml.

Figure 11:
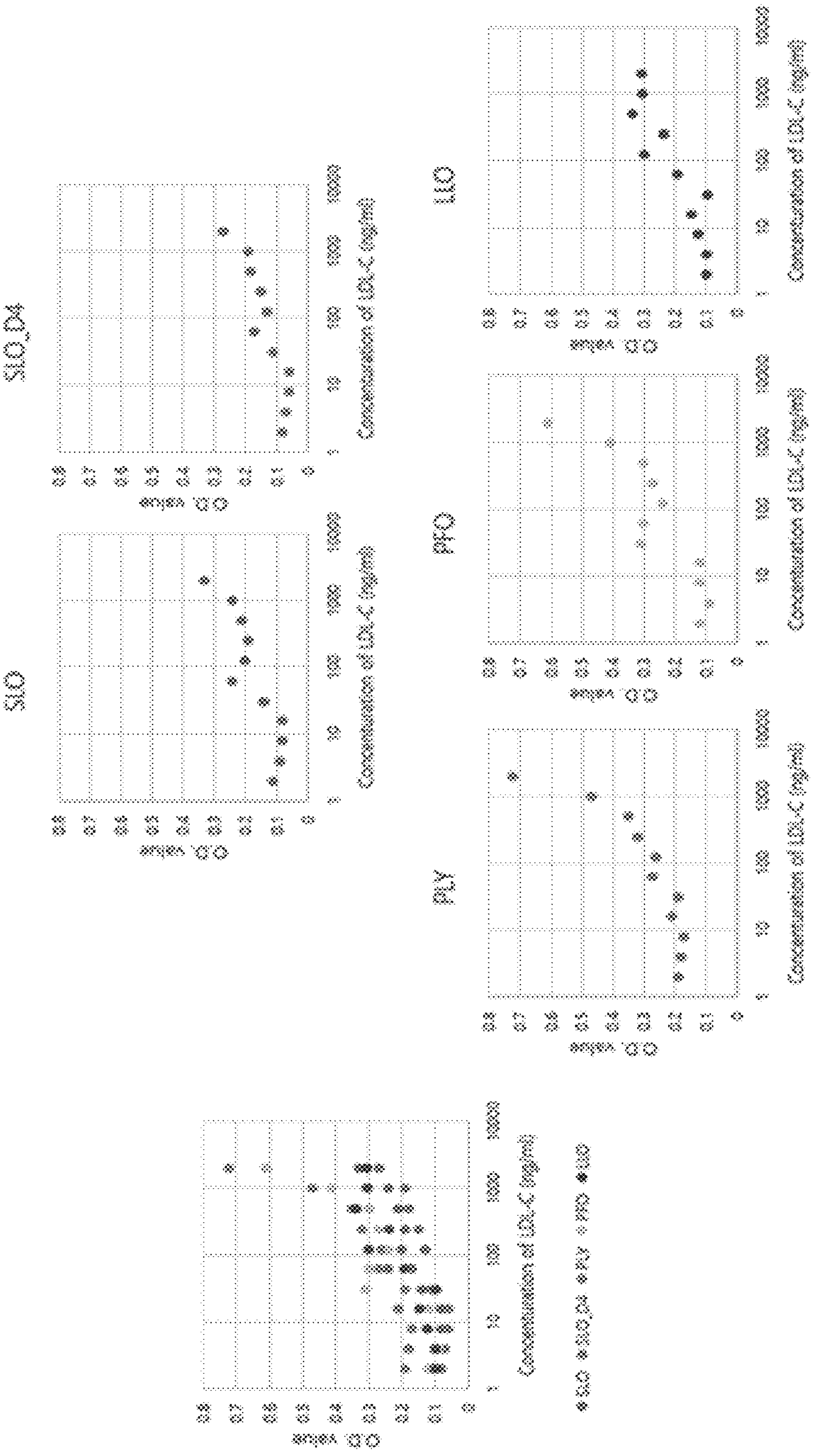
FIG. 11 is a result of measuring the concentration of LDL-C in which cholesterols were bound with CDC (SLO, SLO_D4, LLO, PFO, or PLY) and detected using the antibody #4C2 which recognizes Apo B-100, a main components of LDL-C.

FIG. 11 shows the result of LDL-C concentration measured in which cholesterols present on the surface of lipoproteins were bound to CDC (SLO, SLO_D4, LLO, PFO, PLY) and detected using an antibody #4C2 which recognizes Apo B-100, the main component of LDL-C. This indicates that CDCs when used as a capture are able to detect LDL-C level in a concentration dependent manner upto 60 ng/ml.

3-2. Measurement of Cholesterol Using Rapid Kit

CDC (PLY) fixed on a NC membrane as a capture and LDL antibody (#4C2) as a detection antibody were used to determine the concentration of LDL-C in human serum (n=100).

Specifically, 2.6 mg/ml PLY and 1 mg/ml DNPBSA were applied at 29 mm and 34 mm NC membrane (135), respectively, as a line and the membrane was dried at 37° C. for 1 hour, which was dried again overnight in a desicator with relative humidity of 20% or lower. Then 903 sample pad and T415 absorbent pad were assembled on the membrane.

Selected anti-LDL #4c2 and 0.1M sodium bicarbonate were mixed. Then FPR-648 was added at the weight ratio of Ab:fluorescent=10:1 and incubated at 4° C. overnight. Then antibody conjugated to fluorescent material was then purified using Sephadex G-25. This antibody was then added to DDB to prepare DB.

Figure 12:
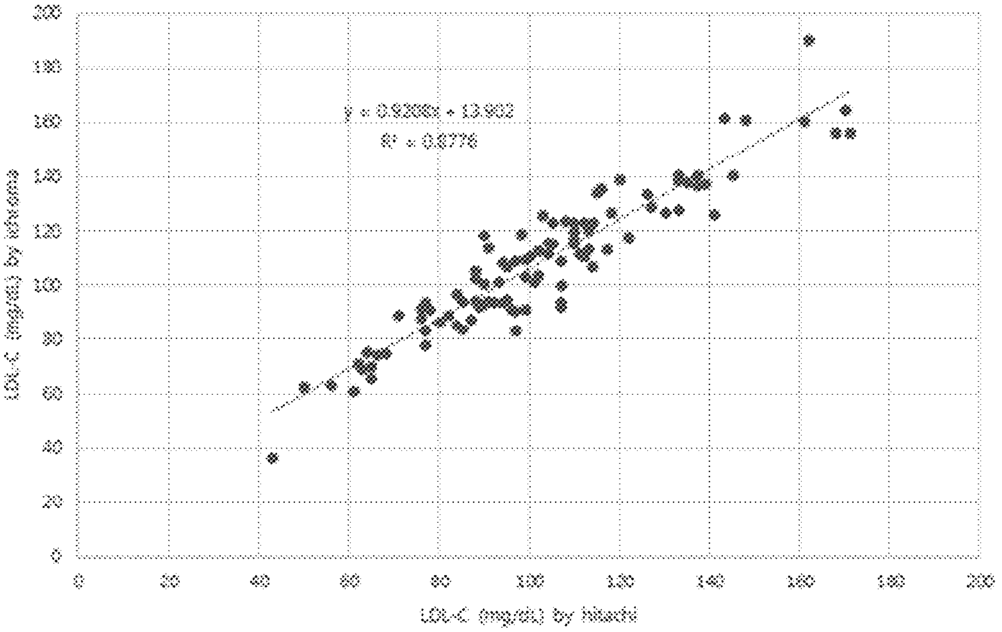
FIG. 12 is a graph showing the correlation of the readings generated from two different systems, in which the cholesterol concentrations were measured from human serum by a rapid kit using CDC protein and anti-LDL antibody prepared in the present disclosure using the measurement method according to one aspect of the present invention, and by a conventional device.

For a cartridge test, 1 μl of a human serum was added to 1000 μl of DB and mixed by shaking 10 times. Then 75 μl of the mixture was applied to the sample pad prepared above and incubated for 15 min. Then the result was analyzed using iChroma® (Boditech Med), in which Hitachi device (Hitachi 7020, Japan) was used as a comparative device and the same test as above was performed. The correlation with the Hitachi device was found to 0.87. The specificity and sensitivity were found to be 88% and 95%, respectively. Results are shown in FIG. 12 and in Table 1 below. The correlation coefficient of 0.87, and the specificity and sensitivity of 88% and 95% indicate that the present method can be efficiently and conveniently used to detect LDL-C in clinic.

TABLE 1

| type | Result | Hitachi Positive | Hitachi Negative | Specificity (%) | Sensitivity (%) |
|---|---|---|---|---|---|
| i-chroma | Positive | 15 | 4 | 88 | 95 |
|  | Negative | 2 | 79 |  |  |
| Sum |  | 100 |  |  |  |

What is claimed is:

1. A method of measuring cholesterol level in a blood sample in vitro, the method comprising:

contacting the sample in need of determination of the cholesterol level with a CDC (Cholesterol Dependent Cytolysin) as a cholesterol binding protein to form a first complex between a lipoprotein, cholesterol and the CDC;

contacting the first complex with an anti-apolipoprotein antibody to form a second complex comprising the lipoprotein, the cholesterol, the CDC and the antibody; and detecting the second complex.

2. A method of measuring the cholesterol level in a blood sample in vitro, the method comprising:

contacting the sample in need of determination of the cholesterol level with an anti-apolipoprotein antibody to form a first complex between a lipoprotein and the antibody;

contacting the first complex with a CDC (Cholesterol Dependent Cytolysin) as a cholesterol binding protein to form a second complex comprising the lipoprotein, cholesterol, the antibody, and the CDC; and detecting the second complex.

3. The method of claim 2, wherein the CDC is selected from the group consisting of ALO (Anthrolysin O) from *Bacillus anthracis*; TLO (Thuringiensilysin O) from *B. thurigiensis*; CLO (Cereolysin O) from *B. cereus*; WLO (Weihenstephanensilysin) from *B. weihenstephanensis*; LLO (Listeriolysin O) from *Listeria monocytogenes*; LSO (Seeligeriolysin O) from *L. seeligeri*; ILO (Ivanolysin) from *L. ivanovii*; SPH (Sphaericolysin) from *Lysinibacillus sphaericus*; ALV (Alveolysin) from *Paenibacillus alvei*; BVL (Brevilysin) from *Brevibacillus* brevi); SLOe (Streptolysin Oe) from *Streptococcus dysgalactiae*; SLO (Streptolysin O) from *S. pyogenes*; SLOc (Streptolysin Oc) from *S. canis*; PSY (Pseudopneumolysin) from *S. pseudonemoniae*; PLY (Pneumolysin) from *S. pneumoniae*; MLY (Mitilysin) from *S. mitis*; SLY (Suilysin) from *S. suis*; ILY (Intermedilysin) from *S. intermedius*; LLY (Lectinolysin) from *S. mitis*; PFO (Perfringolysin O) from *Clostridium perfringens*; BRY (Butyriculysin) from *C. butyricum*; TLY (Tetanolysin O) from *C. tetani*; BLYb (Botulinolysin B) from *C. botulinum* B; BLYe (Botulinolysin E3) from *C. botulinum* E3; BLYc from *C. botulinum* C (Botulinolysin C); NVL (Novyilysin) from *C. novyi*; VLY (Vaginolysin) from *Gardenella vaginallis*; and PLO (Pyolysin) from *Arcanobacterium pyogenes*.

4. The method of claim 2, wherein the anti-apolipoprotein antibody is an anti-LDL antibody or an anti-HDL antibody.

5. The method of claim 2, wherein the sample is a whole blood, a plasma or a serum.

6. The method of claim 2, wherein one of the CDC and the anti-apolipoprotein antibody are fixed on a solid support and the other is labelled with a detectable material.

7. The method of claim 2, wherein the method is performed by ELISA or a lateral flow assay.

8. The method of claim 2, wherein the CDC is fixed on a solid support in advance of contacting the sample with the anti-apolipoprotein antibody, and the antibody is an anti-apolipoprotein B-100 antibody or an anti-apolipoprotein A-1 antibody, and the antibody is labelled with a detectable material.

9. The method of claim 3, wherein the CDC is LLO (Listeriolysin O), PFO (Perfringolysin O), PLY (Pneumolysin), or SLO (Streptolysin O) or SLO-4 (Domain 4 of Streptolysin O).

10. The method of claim 4, wherein the antibody is an anti-apolipoprotein B-100 antibody or an anti-apolipoprotein A-1 antibody.

11. The method of claim 6, wherein the CDC is fixed on a solid support and the antibody is labelled with a detectable material.

12. The method of claim 6, wherein the solid support is beads, membranes, slides, or microtiter plates, made of glass, polystyrene, polysaccharide, nylon or nitrocellulose.

13. The method of claim 6, wherein the detectable material is one or more selected from the group consisting of a fluorescent moiety, a chemiluminescent moiety, a bioluminescence moiety, a magnetic particle, an enzyme, a substrate, a radioisotope and a chromophore.

14. The method of claim 11, wherein the CDC is fixed on a solid support in advance of contacting the sample with the anti-apolipoprotein antibody.

15. The method of claim 13, wherein the detectable material is one or more selected from the group consisting of a radioisotope which is $^{3}H$ or $^{125}I$, fluorescent materials, chemiluminescent materials, hapten, biotin, digoxigenin, a horseradish peroxidase, an alkaline phosphatase, and a maleate dehydrogenase.

16. A lateral flow or ELISA assay kit for measuring cholesterol level in blood comprising CDC (Cholesterol Dependent Cytolysin) as a cholesterol binding protein and an anti-apolipoprotein antibody, wherein the CDC is fixed on a solid support and the antibody is labeled with a detectable material.

17. The kit of claim 16, wherein the anti-apolipoprotein antibody is an anti-LDL antibody or an anti-HDL antibody.

18. The kit of claim 16, wherein the kit is a lateral flow assay kit, and the CDC is fixed on a solid support, and the antibody is an anti-apolipoprotein B-100 antibody or an anti-apolipoprotein A-1 antibody and is labelled with a detectable material.

* * * * *

SEQUENCE LISTING

<160> NUMBER OF SEQ ID NOS: 5

<210> SEQ ID NO 1
<211> LENGTH: 1425
<212> TYPE: DNA
<213> ORGANISM: Artificial Sequence
<220> FEATURE:
<223> OTHER INFORMATION: rPLY in pET21a vector

<400> SEQUENCE: 1
ggatccatgg ccaataaagc agtcaatgat tttatattgg caatgaacta tgataaaaag 60
aaactgctta ctcaccaggg cgagagcatt gagaacagat ttataaaaga ggggaaccaa 120
ctgcccgatg aatttgtggt tatcgagcgt aagaaacgta gcctgtccac aaatacgagc 180
gatatttccg taacagccac gaatgattcc cggctgtacc cgggcgcgct gctggttgtt 240
gacgagaccc tgctggaaaa caatccgact ctgctggcgg tagaccgcgc cccaatgact 300
tattcgatcg acctgccggg tttggcttct agcgatagtt tcctgcaggt ggaagatcca 360
tcaaacagct cggtgcgtgg cgccgttaat gatctgcttg cgaaatggca tcaggattat 420
ggacaggtta acaatgtgcc tgctcgcatg cagtatgaaa aaatcaccgc acattctatg 480
gaacaactca aagttaaatt cgggtcagac tttgaaaaga ccggtaatag cctggatata 540
gactttaatt cggtccatag cggtgaaaag cagattcaga tcgtaaattt caaacaaatt 600
tactatacag tgtctgtcga tgcagtaaaa aaccctggag atgtatttca agacaccgtc 660
acagtggagg acctgaagca gcgcggtatt agcgctgagc gaccgctggt gtatattagc 720
agcgttgctt acggccgtca ggtttatctg aaactcgaaa cgaccagcaa aagcgatgaa 780
gtggaagccg cattcgaagc gctgatcaaa ggtgtcaaag ttgctccaca gacagaatgg 840
aaacagattc tggacaacac ggaagtcaag gcggtgatat taggcggtga tccgagctca 900
ggagcccgcg ttgttacggg aaaagttgat atggttgaag acctaatcca ggaaggttca 960
cggtttactg ccgaccaccc aggtctgcct attagttata ctacgtcctt tctgcgtgac 1020
aatgtcgtag cgactttcca aaatagcacc gattatgttg agacaaaggt gaccgcatat 1080
cgtaacggtg atttactgct tgatcatagt ggggcttatg tagcacaata ctatattacg 1140
tggaatgaat tgtcttacga tcatcagggc aaagaagtac tgacccctaa agcgtgggat 1200
cgtaatggtc aggatttaac ggcacatttt acaacctcga tcccgttgaa ggggaatgtg 1260
agaaacctct ctgtaaaaat ccgcgaatgt acaggcctgg cctgggaatg gtggcgaact 1320
gtttacgaga aaactgatct tccgctggtc cgtaagcgta caatatccat ttggggcacc 1380
accctgtatc cccaagtgga ggacaaagtg gagaacgatc tcgag 1425

<210> SEQ ID NO 2
<211> LENGTH: 1425
<212> TYPE: DNA
<213> ORGANISM: Artificial Sequence
<220> FEATURE:
<223> OTHER INFORMATION: rPFO in pET28a vector

<400> SEQUENCE: 2
ggatccgaca tcaccgataa aaatcagtcg atagacagcg ggattagcag cctgagctat 60
aatcgtaatg aggtactggc tagcaatggc gataaaattg aaagctttgt cccgaaagaa 120
ggtaagaaga ccggtaataa atttatcgtg gtggagagac aaaaacggag cctgaccacg 180
tcgccggtgg atattagcat tatcgatagc gttaatgacc gtacctatcc aggagcactt 240
cagctggcag acaaagcttt cgtagaaaac cgcccgacca tcctgatggt aaaacgtaag 300

```
cccattaata taaacataga cctgccaggc ctgaaaggcg aaaacagcat taaagtcgac    360

gatcccacct acggaaaagt tagcggtgcg attgatgagc tggtttccaa atggaatgag    420

aaatatagca gcactcatac actgccggcg cgcacccaat atagcgaatc catggtctat    480

tcgaaaagcc agatcagcag cgcactcaac gtcaacgcaa aggtcctcga aaatagcctg    540

ggtgtggatt tcaacgctgt agctaacaac gagaagaaag ttatgatcct ggcctacaag    600

caaatttttt atacagtgag cgcggatctg ccgaaaaatc ctagcgatct gtttgacgat    660

agcgtgacat ttaacgatct gaagcagaaa ggcgtttcca atgaagcgcc gcctctgatg    720

gttagcaatg tggcctacgg gcgtaccata tatgttaaac tggaaacgac gagcagcagc    780

aaagatgttc aggccgcatt caaagccctg attaagaaca ccgacataaa aaatagccag    840

cagtacaaag atatttatga gaattccagc ttcaccgccg tggtcttagg cggtgatgct    900

caggaacaca ataaagtagt aacgaaggat ttcgacgaaa tacgtaaagt tatcaaagat    960

aacgcgacct ttagcacgaa aaatccagct tatccgatta gctataccag cgtttttctt   1020

aaggataaca gcgttgccgc agtgcataat aaaaccgatt acatcgagac cacctcaacc   1080

gagtacagca aggggaaaat caatctggac catagcggcg catatgtggc acagtttgaa   1140

gtcgcgtggg acgaagtaag ctacgataag gaagggaatg aagtgctgac gcataagacc   1200

tgggatggta actatcaaga taaaaccgcc cactatagca cggtcatccc gttggaagcg   1260

aatgcgcgca acattcgtat caaagctcgc gagtgtaccg gtctggcctg ggagtggtgg   1320

cgggacgtta tttcggaata tgatgttccc ctgaccaata atattaacgt gtccatatgg   1380

ggaaccaccc tgtaccctgg ctcaagcatt acctataacc tcgag                   1425
```

```
<210> SEQ ID NO 3
<211> LENGTH: 1476
<212> TYPE: DNA
<213> ORGANISM: Artificial Sequence
<220> FEATURE:
<223> OTHER INFORMATION: rLLO in into pET21a vector

<400> SEQUENCE: 3

ggatccatgg cgccgccggc aagcccccct gccagcccga aaactccaat tgagaagaag     60

catgcggacg aaattgataa gtacatccag ggcctggatt acaataaaaa taacgtcctt    120

gtgtatcacg gtgacgcagt aaccaatgtt cctccgcgca agggttataa agatgggaat    180

gaatacatcg tggtggaaaa aaaaaaaaaa tcgataaacc aaaacaacgc agatattcag    240

gtcgttaatg ctatctcaag tctgacatat ccgggtgccc tggtcaaagc taatagcgaa    300

ctggtcgaga accagcccga tgtactgccg gtaaaacgtg acagcctgac tctgagcata    360

gatctgccgg gaatgaccaa ccaagacaac aaaattgtgg ttaaaaatgc taccaagagt    420

aatgtgaata atgctgtgaa cacacttgtt gagcggtgga acgaaaagta tgcgcaggct    480

tacccgaacg taagcgcaaa aattgattat gacgatgaga tggcatatag cgaaagccag    540

ttgattgcca aattcggcac ggccttcaaa gcagttaaca actcgctgaa cgtaaacttt    600

ggtgcgattt ccgaaggcaa aatgcaggag gaagttatat catttaaaca gatctattac    660

aacgttaatg tgaacgagcc gacacgcccg tcccgttttt ttggaaaagc cgttaccaag    720

gaacaactgc aggccctggg cgtcaacgcg gaaaacccgc cggcgtatat cagcagcgtg    780

gcctatgggc gccaggttta cctgaaactc agcacgaaca gccacagcac taaagtaaaa    840

gccgcgtttg atgcagctgt tagcggaaag agcgtgtccg ggatgtcgga actcacaaac    900
```

-continued

```
atcattaaga acagctcgtt taaagccgtg atttatggcg gtagcgcaaa agacgaggtg    960

cagataatcg atgggaacct gggcgacctg cgtgatattc tgaagaaagg cgctaccttc   1020

aacagagaga ccccaggtgt cccgattgca tatactacca acttcctgaa agataacgaa   1080

ctggcagtaa ttaaaaacaa ctccgaatat atcgaaacaa cgagcaaggc ctatacggac   1140

gggaaaatca acattgatca ttcaggtggt tacgtggcgc agtttaatat aagctgggat   1200

gaaattaact atgacccgga aggaaatgag atagttcaac ataagaactg gagcgagaat   1260

aacaaaagca aattggctca ttttaccagc agcatatacc tgcctggcaa tgcgcgtaac   1320

atcaacgttt atgccaaaga atgtaccggt ctggcgtggg aatggtggcg cacggttatc   1380

gacgatcgca acctgcccct ggtgaagaac cggaatatta gcatttgggg caccactctg   1440

tacccgaaat actctaactc ggtcgataac ctcgag                             1476


<210> SEQ ID NO 4
<211> LENGTH: 426
<212> TYPE: DNA
<213> ORGANISM: Artificial Sequence
<220> FEATURE:
<223> OTHER INFORMATION: SLO D4 in pET100 vector

<400> SEQUENCE: 4

catatgcggg gttctcatca tcatcatcat catggtatgg ctagcatgac tggtggacag     60

caaatgggtc gggatctgta cgacgatgac gataaggatc atcccttcac cggcaaaatc    120

aatctgagcc atcgtggtgc atatgttgcc cagtatgaaa ttctgtggga tgagatcaac    180

tatgatgaca aaggcaaaga ggtgattacc aaacgtcgtt gggataataa ctggtatagc    240

aaaaccagcc cgtttagcac cgttattccg ctgggtgcaa atagccgtaa tattcgtatt    300

atggcacgtg aatgtaccgg tctggcatgg gaatggtggc gtaaagttat tgatgaacgt    360

gatgtgaaac tgagcaaaga aatcaacgtg aatattagcg gtagcaccct gagcccgtat    420

ggttaa                                                               426


<210> SEQ ID NO 5
<211> LENGTH: 1500
<212> TYPE: DNA
<213> ORGANISM: Artificial Sequence
<220> FEATURE:
<223> OTHER INFORMATION: SLO gene in pET21a vector

<400> SEQUENCE: 5

ggatccatgc cactagaatc tgcagaaaaa gaagaaaaaa agtcagaaga caaaaaaaag     60

agcgaagaag atcacactga agaaatcaat gacaagattt attcactaaa ttataatgag    120

cttgaagtac ttgctaaaaa tggtgaaacc attgaaaatt ttgttcctaa agaaggcgtt    180

aagaaagctg ataaatttat tgtcattgaa agaaagaaaa aaaatatcaa cactacacca    240

gtcgatattt ccattattga ctctgtcact gataggacct atccagcagc ccttcagctg    300

gctaataaag gttttaccga aaacaaacca gacgcggtag tcaccaagcg aaacccacaa    360

aaaatccata ttgatttacc aggtatggga gacaaagcaa cggttgaggt caatgaccct    420

acctatgcca atgtttcaac agctattgat aatcttgtta accaatggca tgataattat    480

tctggtggta atacgcttcc tgccagaaca caatatactg aatcaatggt atattctaag    540

tcacagattg aagcagctct aaatgttaat agcaaaatct tagatggtac tttaggcatt    600

gatttcaagt cgatttcaaa aggtgaaaag aaggtgatga ttgcagcata caagcaaatt    660

ttttacaccg tatcagcaaa ccttcctaat aatcctgcgg atgtgtttga taaatcagtg    720
```

-continued

```
acctttaaag agttgcaacg aaaaggtgtc agcaatgaag ctccgccact ctttgtgagt    780

aatgtagcct atggtcgaac tgtttttgtc aaactagaaa caagttctaa aagtaatgat    840

gttgaagcgg cctttagtgc agctctaaaa ggaacagatg ttaaaacgaa tggaaaatac    900

tctgatatct tagaaaatag ttcatttaca gctgtcgttt taggaggaga tgctgcagag    960

cacaataagg tagtcacaaa agactttgat gttattagaa acgttatcaa agacaatgct   1020

accttcagta gaaaaaaccc agcttatcct atttcataca ccagtgtttt ccttaaaaat   1080

aataaaattg cgggtgtcaa taacagaact gaatacgttg aaacaacatc taccgagtac   1140

actagtggaa aaattaacct gtctcatcga ggcgcgtatg ttgctcaata tgaaatcctt   1200

tgggatgaaa tcaattatga tgacaaagga aaagaagtga ttacaaaacg acgttgggac   1260

aacaactggt atagtaagac atcaccattt agcacagtta tcccactagg agctaattca   1320

cgaaatatcc gtatcatggc tagagagtgc accggcttag cttgggaatg gtggcgaaaa   1380

gtgatcgacg aaagagatgt gaaactgtct aaagaaatca atgtcaacat ctcaggatca   1440

accctgagcc catatggtta gattacttat aagtaggaat tcgagctccg tcgacaagct   1500
```